United States Patent
Walters et al.

(10) Patent No.: US 9,552,462 B2
(45) Date of Patent: Jan. 24, 2017

(54) METHOD FOR PREDICTING COMPOSITION OF PETROLEUM

(75) Inventors: Clifford C. Walters, Milford, NJ (US); Howard J. Freund, Neshanic Station, NJ (US); Simon R. Kelemen, Annandale, NJ (US); Paul J. Hicks, Jr., Spring Valley, TX (US)

(73) Assignee: ExxonMobil Upstream Research Company, Houston, TX (US)

( * ) Notice: Subject to any disclaimer, the term of this patent is extended or adjusted under 35 U.S.C. 154(b) by 771 days.

(21) Appl. No.: 12/573,428

(22) Filed: Oct. 5, 2009

(65) Prior Publication Data

US 2010/0155078 A1   Jun. 24, 2010

Related U.S. Application Data

(60) Provisional application No. 61/140,249, filed on Dec. 23, 2008.

(51) Int. Cl.
*E21B 41/00* (2006.01)
*G06F 19/00* (2011.01)

(52) U.S. Cl.
CPC ............ *G06F 19/704* (2013.01); *E21B 41/00* (2013.01); *G06F 19/707* (2013.01)

(58) Field of Classification Search
None
See application file for complete search history.

(56) References Cited

U.S. PATENT DOCUMENTS

| | | |
|---|---|---|
| 5,040,414 A | 8/1991 | Graebner |
| 5,159,833 A | 11/1992 | Graebner |
| 5,586,082 A | 12/1996 | Anderson et al. |
| 5,757,663 A | 5/1998 | Lo et al. |
| 5,774,381 A | 6/1998 | Meier |
| 5,798,982 A | 8/1998 | He et al. |
| 5,835,882 A | 11/1998 | Vienot et al. |
| 5,905,657 A | 5/1999 | Celniker |
| 6,013,172 A | 1/2000 | Chang et al. |
| 6,246,963 B1 | 6/2001 | Cross et al. |
| 6,393,906 B1 | 5/2002 | Vityk et al. |

(Continued)

FOREIGN PATENT DOCUMENTS

| | | |
|---|---|---|
| GB | 2 145 508 A | 12/2005 |
| WO | WO 83/03676 | 10/1983 |

(Continued)

OTHER PUBLICATIONS

Barton, A.F.M., (1991) "CRC Handbook of Solubility Parameters and Other Cohesive Parameters" CRC Press, Boca Raton, FL., Chpt. 4, pp. 58-66.

(Continued)

*Primary Examiner* — Angela M DiTrani

(74) *Attorney, Agent, or Firm* — ExxonMobil Upstream Research Company-Law Department

(57) ABSTRACT

A method for predicting petroleum expulsion. A chemical structure of a kerogen is defined and a plurality of reaction products of the kerogen under geologic heating rates are identified. The plurality of reaction products are grouped into a plurality of product lumps based on their chemical composition and predicting petroleum expulsion for each of the plurality of product lumps based on secondary cracking reactions.

24 Claims, 11 Drawing Sheets

(56) References Cited

U.S. PATENT DOCUMENTS

| | | |
|---|---|---|
| 6,514,915 B1 | 2/2003 | Beyer et al. |
| 6,661,000 B2 | 12/2003 | Smith et al. |
| 6,754,588 B2 | 6/2004 | Cross et al. |
| 6,810,332 B2 | 10/2004 | Harrison |
| 6,826,483 B1 | 11/2004 | Anderson et al. |
| 6,950,751 B2 | 9/2005 | Knobloch |
| 6,985,841 B2 | 1/2006 | Barroux |
| 7,124,030 B2 | 10/2006 | Ellis |
| 7,174,254 B2 | 2/2007 | Ellis |
| 7,210,342 B1 | 5/2007 | Sterner et al. |
| 7,249,009 B2 | 7/2007 | Ferworn et al. |
| 7,297,661 B2 | 11/2007 | Beyer et al. |
| 7,337,660 B2 | 3/2008 | Ibrahim et al. |
| 7,344,889 B2 | 3/2008 | Kelemen |
| 7,387,021 B2 | 6/2008 | DiFoggio |
| 7,395,691 B2 | 7/2008 | Sterner et al. |
| 7,520,158 B2 | 4/2009 | DiFoggio |
| 7,526,418 B2 | 4/2009 | Pita et al. |
| 7,529,626 B1 | 5/2009 | Ellis |
| 8,352,228 B2 | 1/2013 | Walters et al. |
| 2002/0013687 A1 | 1/2002 | Ortoleva |
| 2002/0049575 A1 | 4/2002 | Jalali |
| 2002/0067373 A1 | 6/2002 | Roe |
| 2002/0099504 A1 | 7/2002 | Cross |
| 2002/0120429 A1 | 8/2002 | Ortoleva |
| 2004/0148147 A1 | 7/2004 | Martin |
| 2004/0210547 A1 | 10/2004 | Wentland et al. |
| 2004/0220790 A1 | 11/2004 | Cullick et al. |
| 2004/0254734 A1 | 12/2004 | Zabalza-Mezghani |
| 2005/0096893 A1 | 5/2005 | Feraille |
| 2005/0149307 A1 | 7/2005 | Gurpinar |
| 2005/0199391 A1 | 9/2005 | Cudmore |
| 2005/0209866 A1 | 9/2005 | Veeningen |
| 2005/0209912 A1 | 9/2005 | Veeningen |
| 2005/0234690 A1 | 10/2005 | Mainguy et al. |
| 2005/0256647 A1 | 11/2005 | Ellis |
| 2006/0014647 A1 | 1/2006 | Beyer et al. |
| 2006/0041409 A1 | 2/2006 | Strebelle |
| 2006/0047489 A1 | 3/2006 | Scheidt et al. |
| 2006/0052938 A1 | 3/2006 | Thorne |
| 2006/0092766 A1 | 5/2006 | Shelley |
| 2006/0235667 A1 | 10/2006 | Fung et al. |
| 2006/0235668 A1 | 10/2006 | Swanson et al. |
| 2006/0241867 A1 | 10/2006 | Kurchuk |
| 2006/0265204 A1 | 11/2006 | Wallis |
| 2006/0277012 A1 | 12/2006 | Ricard et al. |
| 2006/0277013 A1 | 12/2006 | Bennis |
| 2006/0282243 A1 | 12/2006 | Childs et al. |
| 2006/0287201 A1 | 12/2006 | Georgi |
| 2006/0293872 A1 | 12/2006 | Zamora |
| 2007/0005253 A1 | 1/2007 | Fornel |
| 2007/0011646 A1 | 1/2007 | Chrisochoides |
| 2007/0013690 A1 | 1/2007 | Grimaud |
| 2007/0016389 A1 | 1/2007 | Ozgen |
| 2007/0143024 A1 | 6/2007 | Michel |
| 2007/0156377 A1 | 7/2007 | Gurpinar |
| 2007/0219724 A1 | 9/2007 | Li et al. |
| 2007/0219725 A1 | 9/2007 | Sun |
| 2007/0242564 A1 | 10/2007 | Devi |
| 2007/0265778 A1 | 11/2007 | Suter |
| 2008/0040086 A1 | 2/2008 | Betancourt et al. |
| 2008/0059140 A1* | 3/2008 | Salmon et al. ............ 703/12 |
| 2008/0097735 A1 | 4/2008 | Ibrahim et al. |
| 2008/0099241 A1 | 5/2008 | Ibrahim et al. |
| 2008/0147326 A1 | 6/2008 | Ellis |
| 2008/0173804 A1 | 7/2008 | Indo et al. |
| 2009/0071239 A1 | 3/2009 | Rojas et al. |

FOREIGN PATENT DOCUMENTS

| | | |
|---|---|---|
| WO | WO03/093815 | 11/2003 |
| WO | WO2004/102156 | 11/2004 |
| WO | WO2007/007210 | 1/2007 |
| WO | WO2007/063442 | 6/2007 |
| WO | WO2008/100614 | 8/2008 |
| WO | WO 2009/094064 | 7/2009 |
| WO | WO2010/008647 | 1/2010 |

OTHER PUBLICATIONS

Behar, F., et al., (2007) "New IFP compositional kinetics of oil generation and degradation" AAPG Hedberg Research Conference (The Hague, The Netherlands, May 6-9, 2007).

Duppenbecker, S.J., et al., (1991) "Numerical modeling of petroleum expulsion in two areas of the Lower Saxony Basin, northern Germany" *Petroleum migration, Geological Society Special Publications 59, 59* W.A. England, A.J. Fleet, ed., Geological Society of London, London, United Kingdom, pp. 47-64.

Durand, B., et al., (1987) "Oil saturation and primary migration; observations in shales and coals from the Kerbau wells, Mahakam Delta, Indonesia" In: *Migration of Hydrocarbons in Sedimentary Basins, 2nd IFP Exploration Research Conference, 45* B. Doligez, ed., Technip, Paris, France, Carcans, France, pp. 173-195.

Espitalié, J., et al., (1993) "Critical study of kinetic modelling parameters" In: A.G. Dore, J.H. Augustson, C. Hermanrud and D.J. Stewart (Eds.), Basin Modelling: Advances and Applications, Norwegian Petroleum Society' Special Publication 3. Elsevier, pp. 233-242.

Fedors, R.F. (1974), "A Method for Estimating Both the Solubility Parameters and Molar Volumes of Liquids", Polymer Engineering & Science, v. 14, No. 2, pp. 147-155.

Flory, P.J., (1953) Principles of Polymer Chemistry. Cornell University Press, Ithaca, NY, pp. 576-581.

Freund, H., et al., (2005) "Predicting Oil and Gas Compositional Yields from First Principles, chemical yield modeling (CSCYM), Part 1, Concepts & Implementation" Organic Chemistry, 38, pp. 288-305.

Hansen, C.M., (1967) "The three dimensional solubility parameter—key to paint component affinities: I. Solvents plasticizers, polymers, and resins" Journal of Paint Technology 3, pp. 104-117.

Hsieh, S.T., Duda, J.L., (1987) "Probing coal structure with organic vapor sorption" Fuel 66, 170-178.

Isaacs, C.M., (2001) "Depositional framework of the Monterey Formation, California" *The Monterey Formation: From Rocks to Molecules* C.M. Isaacs, J. Rullkätter, ed., Columbia University Press, New York, pp. 1-30.

Justwan, H.K., et al., (2008) "Unraveling dynamic fluid connectivity through time-lapse geochemistry—from example from the Ringhorne Field, Norway," AAPG Int'l. Conf and Exhibition, Cape Town, South Africa.

Lafargue, E., et al., (1994). "Experimental simulation of primary migration" Organic Geochemistry 22, pp. 575-586.

Larsen, J.W., et al., (1990) "Solvent swelling studies of two low-rank coals" Energy & Fuels 4, pp. 74-77.

Larsen, J.W., et al., (1994) "Solvent swelling studies of Green River kerogen" Energy & Fuels 8, pp. 932-936.

Lucht, L.M., et al., (1987) "Macromolecular structure of coals .3. Equilibrium swelling of coal particles in various solvents". Erdol & Kohle Erdgas Petrochemie 40, pp. 483-485.

Mann, U., (1990) "Sedimentological and petrophysical aspects of primary petroleum migration pathways" In: *Sediments and environmental geochemistry; selected aspects and case histories* D. Heling, P. Rothe, U. Foerstner, P. Stoffers, ed., pp. 152-178. Springer-Verlag, Berlin, Federal Republic of Germany.

Mann, U., et al., (1991) "Pore network evolution of the Lower Toarcian Posidonia Shale during petroleum generation and expulsion; a multidisciplinary approach. New approaches in exploration geology" Kontaktwochenende/Rheinisch-Westfaelische Technische Hochschule Aachen; New approaches in exploration geology 1990, pp. 1051-1071.

Palciauskas, V.V., et al., (1991) "Primary migration of petroleum Source and migration processes and evaluation techniques" AAPG treatise of petroleum geology; handbook of petroleum geology. Am. Assoc. Pet. Geol., Tulsa, OK, United States, Chapter 2, pp. 13-22.

Sanada, Y., Honda, H., (1966) "Swelling equilibrium of coal by pyridine at 25°" Fuel 45, pp. 295-300.

(56) References Cited

OTHER PUBLICATIONS

Sassen, R., et al., (1987) "Distribution of hydrocarbon source potential in the Jurassic Smackover Formation" Organic Geochemistry 11, pp. 379-383.

Talukdar, S.N., et al., (1987) "Observations on the primary migration of oil in the La Luna source rocks of the Maracaibo Basin, Venezuela. Migration of hydrocarbons in sedimentary basins" 2nd IFP exploration research conference 45, pp. 59-77.

Tissot, B. P. et al., (1984) "Petroleum Formation and Occurrence", second edition, Springer-Verlag, Berlin, pp. 151.

Tissot, B., (1987) "Migration of hydrocarbons in sedimentary basins; a geological, geochemical and historical perspective". *Migration of Hydrocarbons in Sedimentary Basins, $2^{nd}$ IFP Exploration Research Conference*, 45 B. Doligez, ed., Technip, Paris, France, Carcans, France, pp. 1-19.

Welte D. H., et al., (1997) "Petroleum and Basin Evolution: Insights from Petroleum Geochemistry", Geology and Basin Modeling, Springer, pp.

Sandvik, E.I., et al., (1992) "Expulsion from hydrocarbon sources; the role of organic absorption. Advances in organic geochemistry 1991; Part 1, Advances and applications in energy and the natural environment" Proceedings of the 15th international meeting on Organic geochemistry 19, 77-87.

Snedden, J.W. et al., (2007) "Reservoir Connectivity: Definitions, Examples, and strategies," IPTC Conference proceedings Dubai, U.A.E., No. 11375, pp. 1-22.

Stainforth, J.G., et al., (1990) "Primary migration of hydrocarbons by diffusion through organic matter networks, and its effect on oil and gas generation" Organic Geochemistry 16, 61-74.

Stainforth, et al (2009) "Practical kinetic modeling of petroleum generation and expulsion" Marine and Petroleum Geology, Gutterworth Scientific, Guildford, GB vol. 26, No. 4 pp. 552-572 ISSN: 0264-8172.

Sumpter, L. et al., (2008) "Early Recognition of Potential Reservoir Compartmentalization," Reservoir Compartmentalization, London Geological Society, Mar. 5-6, 2008, p. 84.

Sweeney, J.J., et al., (1995) "Chemical kinetic model of hydrocarbon generation, expulsion, and destruction applied to the Maracaibo Basin" Venezuela American Association of Petroleum Geologists Bulletin 79, 1515-1531.

Sweet, M.L., et al., (2007) "Genesis Field, Gulf of Mexico: Recognizing Reservoir Compartments on geologic and production time scales in deep-water reservoirs," AAPG Bulletin, vol. 91 No. 12, pp. 1701-1729.

Tang, Y., et al., (1994) "Multiple cold trap pyrolysis-gas chromatography—a new technique for modeling hydrocarbon generation". Organic Geochemistry 22, 863-872.

Thomas, M.M., et al., (1990) "Primary migration by diffusion through kerogen; III, Calculation of geologic fluxes" Geochimica et Cosmochimica Acta 54, 2793-2797.

Ungerer, P., (1990) "State-of-the-art of research in kinetic modeling of oil formation and expulsion" Organic Geochemistry 16, 1-25.

Ungerer, P., (2003) "From Organic Geochemistry to Statistical Thermodynamics: the Development of Simulation Methods for the Petroleum Industry", Oil and Gas science and Technology—Rev. IFP, vol. 58 (2003) No. 2 pp. 271-297.

Walters, C.C., et al., (2007) Predicting oil and gas compositional yields via chemical structure-chemical yield modeling (CS-CYM): Part 2—Application under laboratory and geologic conditions. Organic Geochemistry 38, 306-322.

Wendebourg, J. (2000), "Modeling multi-component petroleum fluid migration in sedimentary basins", Journal of Geochemical Exploration 69-70, 651-656.

Young, A., et al., (1977). "Distribution of hydrocarbons between oils and associated fine-grained sedimentary rocks-physical chemistry applied to petroleum geochemistry" II. American Association of Petroleum Geologists Bulletin 61, 1407-1436.

European Search Report (Extended) EP 09 15 7938 for Application No. 09157938.3-1266 dated Oct. 29, 2009.

European Search Report (Extended) EP 09 15 7938 for Application No. 09157939.1-1266 dated Oct. 7, 2009.

U.S. Appl. No. 12/573,428, filed Oct. 5, 2009.

U.S. Appl. No. 12/571,937, filed Oct. 1, 2009.

Al Darouich, T., et al., (2006) "Thermal cracking of the light aromatic fraction of Safaniya crude oil—Experimental study and compositional modelling of molecular classes" Organic Geochemistry 37, 1130-1154.

Andresen, B., et al., (1993) "Yields and carbon isotopic composition of pyrolysis products from artificial maturation processes" Chemical Geology 106, 103-119.

Barker, C., (1972) "Aquathermal pressuring: role of temperature in development of abnormal pressure zones" American Association of Petroleum Geologists Bulletin 56, 2068-2071.

Behar, F., et al., (1991) "Experimental simulation in a confined system and kinetic modelling of kerogen and oil cracking" Organic Geochemistry 19, 173-189.

Behar, F., et al., (1995) "Experimental simulation of gas generation from coals and a marine kerogen" Chemical Geology 126, 247-260.

Behar, F., et al., (1997) "Comparison of rate constants for some molecular tracers generated during artificial maturation of kerogens: influence of kerogen type" Organic Geochemistry 26, 281-287.

Behar, F., et al., (1997) "Thermal cracking of kerogen in open and closed systems: determination of kinetic parameters and stoichiometric coefficients for oil and gas generation" Organic Geochemistry 26, 321-339.

Behar, F., et al., (2002) Thermal stability of alkylaromatics in natural systems: Kinetics of thermal decomposition of dodecylbenzene. Energy & Fuels 16, 831-841.

Braun, R.L., et al., (1991) "Pyrolysis kinetics for lacustrine and marine source rocks by programmed micropyrolysis" Energy & Fuels 5, 192-204.

Braun, R.L.,Burnham, A.K., (1992) "PMOD; a flexible model of oil and gas generation, cracking, and expulsion" Organic Geochemistry 19, 161-172.

Burnham, A. K., et al., (1990) "Development of a detailed model of petroleum formation, destruction, and expulsion from lacustrine and marine source rocks" Organic Geochemistry 16, 27-39.

Burnham, A.K., et al., (1999) "Global kinetic analysis of complex materials" Energy & Fuels 13, 1-22.

Cook, A.C., et al., (1991) "Classification of oil shales, coals and other organic-rich rocks" Organic Geochemistry 17, 211-222.

Curry, D.J., et al., (2005) "An integrated multi-component model for petroleum generation and cracking" Book of Abstracts, EAOG $22^{nd}$ International Meetings on Organic Geochemistry. Seville, Spain, Sep. 12-16, 2005.

Dartiguelongue, C., et al., (2006) "Thermal stability of dibenzothiophene in closed system pyrolysis: Experimental study and kinetic modeling" Organic Geochemistry 37, 98-116.

Dieckmann, V., et al., (1998) "Kinetics of petroleum generation and cracking by programmed temperature closed-system pyrolysis of Toarcian shales" Fuel, 77, 23-31.

Dieckmann, V., et al. (2004) Predicting the composition of natural gas generated by the Duvernay Formation (Western Canada Sedimentary Basin) using a compositional kinetic approach, Organic Geochemistry 35, 845-962.

Dieckmann, V., et al., (2006) "A new approach to bridge the effect of organofacies variations on kinetic modelling and geological extrapolations" Organic Geochemistry 37, 728-739.

di Primio, R., et al., (2006) "From petroleum-type organofacies to hydrocarbon phase prediction" American Association of Petroleum Geologist Bulletin 90, 1031-1058.

England, W.A., et al., (1987) "The movement and entrapment of petroleum fluids in the subsurface" Journal of the Geological Society London 144, 327-347.

Ertas, D., et al., (2006) "Petroleum expulsion Part 1. Theory of kerogen swelling in multicomponent solvents" Energy & Fuels 20, 295-300.

Fouch, T.D., et al., (1994). "Green River petroleum system, Uinta Basin, Utah, U.S.A" In: L.B. Magoon and W.G. Dow (Eds.), The Petroleum System; From Source to Trap. AAPG Memoir. American Association of Petroleum Geologists, Tulsa, OK, United States, pp. 399-421.

(56) References Cited

OTHER PUBLICATIONS

Freund, H., (1992) "Application of a detailed chemical kinetic model to kerogen maturation" Energy & Fuels 6, 318-326.
Freund, H., et al., (2007), "Predicting oil and gas compositional yields via chemical structure-chemical yield modeling (CS-CYM): Part 1 Concepts and implementation", Organic Geochemistry 38, 288-305.
Horsfield, B., et al., (1992) "An investigation of the in-reservoir conversion of oil to gas: Compositional and kinetic findings from closed-system programmed-temperature pyrolysis" Organic Geochemistry, 19, 191-204.
Hunt, J.M., (1987) "Primary and secondary migration of oil: Exploration for heavy crude oil and natural bitumen. In: Exploration for heavy crude oil and natural bitumen" 25 (Ed. by R.F. Meyer), pp. 345-349. American Association of Petroleum Geologists, Tulsa, OK, United States, Santa Maria, CA, United States.
Hunt, J.M., (1990) "Generation and migration of petroleum from abnormally pressured fluid compartments" American Association of Petroleum Geologists Bulletin 74, 1-12.
Jarvie, D.M., (1991) "Factors affecting Rock-Eval derived kinetic parameters" Chemical Geology 93, 79-99.
Justwan, H., et al., (2008) "Characterization of Static and Dynamic Reservoir Connectivity for the Ringhorne Field, through integration of Geochemical and engineering data: Reservoir compartmentalization."
Kelemen, S.R., et al., (2005) "Chemical Fractionation During Expulsion Explained by Selectivity Solubility" Oral Presentation in EAOG $22^{nd}$ International Meetings on Organic Geochemistry. Seville, Spain, Sep. 12-16, 2005.
Kelemen, S.R., et al., (2006) "Petroleum expulsion Part 2. organic matter type and maturity effects on kerogen swelling by solvents and thermodynamic parameters for kerogen from regular solution theory", Energy & Fuels 20, 301-308.
Kelemen, S.R., et al., (2006) "Petroleum expulsion Part 3. A model of chemically driven fractionation during expulsion of petroleum from kerogen". Energy & Fuels 20, 309-319.
Khavari-Khorasani, G., et al., (1998) "The factors controlling the abundance and migration of heavy versus light oils, as constrained by data from the Gulf of Suez. Part I. The effect of expelled petroleum composition, PVT properties and petroleum system geometry". Organic Geochemistry 29, 255-282.
Larsen, J.W., et al., (1985) "The nature of the macromolecular network structure of bituminous coals" Journal of Organic Chemistry 50, 4729-4735.
Larsen, J.W., et al., (1991) "Solvent extraction of coals during analytical solvent swelling. A potential source of error" Energy & Fuels 5, 57-59.
Larsen, J.W., et al., (1997) "Changes in the macromolecular structure of a Type I kerogen during maturation" Energy & Fuels 11, 897-901.
Larsen, J.W., et al., (1997) "An initial comparison of the interactions of Type I and III kerogens with organic liquids" Organic Geochemistry 26, 305-309.
Lewan, M.D., et al., (2002) "Comparison of petroleum generation kinetics by isothermal hydrous and nonisothermal open-system pyrolysis" Organic Geochemistry 33, 1457-1475.
Leythaeuser, D et al., (1991) "Expulsion of petroleum from type III kerogen source rocks in gaseous solution; modeling of solubility fractionation" *Petroleum Migration, Geological Society Special Publication 59, 59* W.A. England, A.J. Fleet, ed., pp. 33-46. Geological Society of London, London, United Kingdom.
Liu, J. Z., et al., (1997) "Kinetics of petroleum generation determined from multiple cold trap pyrolysis gas chromatography" Chinese Science Bulletin 42, 254-258.
Manzocchi, et al., (2008) "Sensitivity of the impact of geological uncertainty on production from faulted and unfaulted shallow-marine oil reservoirs: objectives and methods," Petroleum Geoscience, [Online], vol. 14, Feb. 2008, pp. 3-15, XP0024998778.
Palacas, J.G., (1984) "Carbonate rocks as sources of petroleum: Geological and chemical characteristics and oil-source correlations" Proceedings of the Eleventh World Petroleum Congress 1983, London 2, 31-43.
Pepper, A.S., (1991) Estimating the petroleum expulsion behaviour of source rocks; a novel quantitative approach. In: W.A. England and A.J. Fleet (Editors), Petroleum migration, Geological Society Special Publications 59. Geological Society of London, London, United Kingdom, pp. 9-32.
Pepper, A. S., et al., (1995) "Simple kinetic models of petroleum formation; Part III, Modelling an open system", Marine and Petroleum Geology 12, 417-452.
Peters, K.E., et al., (2006) "Evaluation of kinetic uncertainty in numerical models of petroleum generation" American Association of Petroleum Geologists Bulletin 90, 387-403.
Philippi, G.T., (1965) "On the depth, time and mechanism of petroleum generation" Geochimica et Cosmochimica Acta 29, 1021-1049.
Price, L.C., (1989) "Primary petroleum migration from shales with oxygen-rich organic matter" Journal of Petroleum Geology 12, 289-324.
Richards, B., et al., (2008) "Reservoir Connectivity Analysis of a Complex Combination Trap Terra Nova Field, Jeanne d'Arc Basin, Newfoundland, Canada," Reservoir Compartmentalization, London Geological Society, Mar. 5-6, 2008, p. 59.
Ritter, U., (2003) "Solubility of petroleum compounds in kerogen: implications for petroleum expulsion" Organic Geochemistry 34, 319-326.
Ritter, U., et al., (2005) "Adsorption of petroleum compounds in vitrinite: implications for petroleum expulsion from coal" International Journal of Coal Geology 62, 183-191.
Gainski, M. et al. (2008) :"The schiehallion field: detection of reservoir compartmentalization and identification, of new infill targets using 4D seismic surveys and dynamic production data", Abstract from *Reservoir Compartmentalization*, [Online], Mar. 5-6, 2008, P. 32, XP002498777.https://geolsoc.org.uk/~/media/shared/documents/specialist%20and%20regional%20groups/petroleum/Resevoir%20Compartmentalization%20Abstract%20Book%-2056%20March%202008.pdf?la=en; Retrieved from the Internet on Oct. 28, 2016.

\* cited by examiner

METHOD FOR PREDICTING COMPOSITION OF PETROLEUM

CROSS-REFERENCE TO RELATED APPLICATION

This application claims the benefit of U.S. Provisional Patent Application 61/140,249 filed Dec. 23, 2008 entitled METHOD FOR PREDICTING COMPOSITION OF PETROLEUM.

FIELD OF THE INVENTION

Exemplary embodiments of the present invention relate to a method for predicting composition of petroleum generation and expulsion from source rocks. An exemplary embodiment of the present invention takes into account reactions from secondary cracking.

BACKGROUND OF THE INVENTION

This section is intended to introduce various aspects of the art, which may be associated with exemplary embodiments of the present invention. This discussion is believed to assist in providing a framework to facilitate a better understanding of particular aspects of the present invention. Accordingly, it should be understood that this section should be read in this light, and not necessarily as admissions of prior art.

Basin modeling is the process of using either proprietary or commercially available software to assess charge risk by integrating diverse geological and engineering data types into a model of one or more petroleum systems active in an area being explored. The scale of the model may range in size from a single drilling prospect to an entire basin.

There are several commercial basin simulators that are widely used in academia and industry. These known simulators base the kinetics of petroleum generation on some form of a series of parallel first order reactions, usually expressed by the Arrhenius Equation as a discrete spectrum of activation energies ($E_a$). These models comprise a distribution of $E_a$'s at fixed or variable spacing (typically 1 kcal/mole) using a single or varying frequency factor (A). The parameters for these models are based on various laboratory experiments. Some known models rely on simple compositional models that are rooted in a petroleum modeling computer program called PMOD developed and made available by the Lawrence Livermore National Laboratory. Additionally, some models offer compositional yield models based on forms of pyrolysis, including open-system pyrolysis. Other models use a compositional yields model based on open and closed-system pyrolysis. Models that predict compositional yields as defined by varying chemical lumps are expressed typically by the bulk kerogen yield kinetic model (discrete $E_a$'s fixed or varying A) where the percentage of each chemical lump is defined for each individual Ea.

One known basin simulator has models of petroleum generation/expulsion that are either two component (gas/oil) or three component (dry gas/wet gas/oil). Generation is modeled using standard discrete energy kinetics derived from open-system pyrolysis for main-stage oil/gas generation and a late-gas generation model for methane formation from reacted kerogen residue. Both processes are modeled using the first order kinetics with a distributed $E_a$ and fixed A. The expulsion model is based on filling available rock pore space to a defined threshold. Secondary cracking reactions are Oil→Gas in the two-component model or Oil→Wet Gas and Wet Gas→Dry Gas in the three-component model. Hence, only the gas/oil ratio or GOR changes as a function of oil cracking with the oil remaining at a fixed composition and quality. In reality, the composition of petroleum changes in a systematic fashion with increasing thermal stress. Polar compounds and large polynuclear aromatic hydrocarbons or PAH are depleted, while the distribution of the surviving hydrocarbons shifts toward smaller species. The net-effect on oil quality is an increase in American Petroleum Institute gravity (referred to as API gravity herein) and GOR and a decrease in sulfur and nitrogen.

Many known modeling techniques employ data that is derived from laboratory experiments. A potential problem relating to laboratory data involving high temperatures is that the coupled processes of generation, expulsion, and secondary cracking may be perturbed and follow mechanisms and pathways that do not occur under geologic conditions. For example, open system pyrolysis experiments measure gas-phase products that are transported from the source rock place in a heated sample holder to a flame ionization or mass spectrometer detector. Hence, expulsion is controlled mostly by volatility. In closed-system pyrolysis experiments, product yields may be defined in terms of gas-phase volatility, solubility in organic solvents, or as free-floating bitumen in hydrous systems. However, the factors that control petroleum expulsion and chemical fractionation in geologic settings, such as kerogen retention and relative solubilities are typically greatly perturbed by the high temperatures required for generation under observable time intervals (typically less than three days though experiments lasting up to five years have been conducted).

Since expulsion and generation cannot be reliably simulated as a coupled process, laboratory experiments have great difficulty in resolving primary generation from secondary, potentially non-realistic, reactions. In closed system experiments, it is often very difficult to resolve whether the measured products evolve directly from kerogen decomposition or from the thermal cracking of confined products that are not normally retained in a natural system environment. The artificial confinement of metastable species also may promote condensation reactions, forming new organic solids. Open system experiments pose the opposite effect; that is, the rapid removal and quenching or detection of metastable products that may remain in natural systems and undergo secondary cracking reactions. Laboratory simulations typically fail to account accurately the retention that occurs in natural geologic systems at much lower temperatures and removal of products as kerogen matures under geologic conditions. Research has shown that all laboratory artifacts cannot be eliminated and that some models may produce unrealistic bitumen compositions.

If laboratory experiments are inherently flawed, an accurate prediction of the thermal decomposition of kerogen and its product yields rests in constructing a theoretical framework based on fundamental principles. That is, the definition of mechanisms and kinetic rates of elementary reactions, which may be measured with high confidence, to molecular assemblages that reflect the complexity of kerogen. With such a model, it should be possible to predict the generation and expulsion under various laboratory and geologic conditions. While there have been numerous studies that formulated reaction schemes and associated kinetics to explain the results of specific laboratory experiments or field observations, there have been few attempts at constructing a comprehensive model that can account for petroleum generation and expulsion under a wide range of conditions. Some attempts have been made at constructing reaction models that account for product yields from experiments conducted under a variety of laboratory conditions and apply the model to a geologic setting. However, these models are phenomenological and rely on the extrapolation of laboratory-derived kinetics to geologic heating rates. An improved method of modeling basin performance, including predicting petroleum production, is desirable.

SUMMARY OF THE INVENTION

A method for predicting petroleum expulsion is provided. An exemplary embodiment of the method comprises defining a chemical structure of a kerogen and identifying a plurality of reaction products of the kerogen under geologic heating rates. The exemplary method also comprises grouping the plurality of reaction products into a plurality of product lumps based on their chemical composition and predicting petroleum expulsion for each of the plurality of product lumps based on secondary cracking reactions.

In one exemplary method, petroleum expulsion is computed at a plurality of varying heating rates. A production rate curve may be defined for each of the plurality of product lumps. A plurality of stoichiometric coefficients may be defined for each of the plurality of product lumps.

Predicting petroleum expulsion may comprise employing a theoretical model in one exemplary embodiment of the present invention. An exemplary method may comprise comparing predicted petroleum expulsion to known data. The chemical structure may be redefined if the predicted petroleum expulsion is outside a specified range with respect to the known data. According to one exemplary embodiment, an outline of secondary cracking reactions is prepared.

In one exemplary embodiment, predicted petroleum expulsion comprises a quantity of expelled petroleum. Moreover, predicted petroleum expulsion may additionally comprise timing data regarding petroleum expulsion.

One exemplary embodiment of the present invention relates to a method of producing hydrocarbons from an oil and/or gas field. Such an exemplary embodiment may comprise defining a chemical structure of a kerogen deposited in the oil and/or gas field and identifying a plurality of reaction products of the kerogen under geologic heating rates. One exemplary embodiment comprises grouping the plurality of reaction products into a plurality of product lumps based on their chemical composition and predicting petroleum expulsion for each of the plurality of product lumps based on secondary cracking reactions.

Hydrocarbons may be extracted from the oil and/or gas field using the predicted petroleum expulsion. In one exemplary method of producing hydrocarbons, petroleum expulsion is computed at a plurality of varying heating rates. A production rate curve may be defined for each of the plurality of product lumps. A plurality of stoichiometric coefficients may be defined for each of the plurality of product lumps.

Predicting petroleum expulsion may comprise employing a theoretical model in one exemplary embodiment of the present invention. An exemplary method of producing hydrocarbons may additionally comprise comparing predicted petroleum expulsion to known data. The chemical structure may be redefined if the predicted petroleum expulsion is outside a specified range with respect to the known data. According to one exemplary embodiment of a method for producing hydrocarbons, an outline of secondary cracking reactions is prepared.

In one exemplary embodiment of a method for producing hydrocarbons, predicted petroleum expulsion comprises a quantity of expelled petroleum. Moreover, predicted petroleum expulsion may additionally comprise timing data regarding petroleum expulsion.

One exemplary embodiment of the present invention relates to a tangible, machine-readable medium. An exemplary tangible, machine-readable medium comprises code adapted to define a chemical structure of a kerogen and code adapted to identify a plurality of reaction products of the kerogen under geologic heating rates. The exemplary tangible, machine-readable medium may additionally comprise code adapted to group the plurality of reaction products into a plurality of product lumps based on their chemical composition and code adapted to predict petroleum expulsion for each of the plurality of product lumps based on secondary cracking reactions.

DESCRIPTION OF THE DRAWINGS

The foregoing and other advantages of the present invention may become apparent upon reviewing the following detailed description and drawings of non-limiting examples of embodiments in which.

DETAILED DESCRIPTION OF THE INVENTION

Figure 1A:
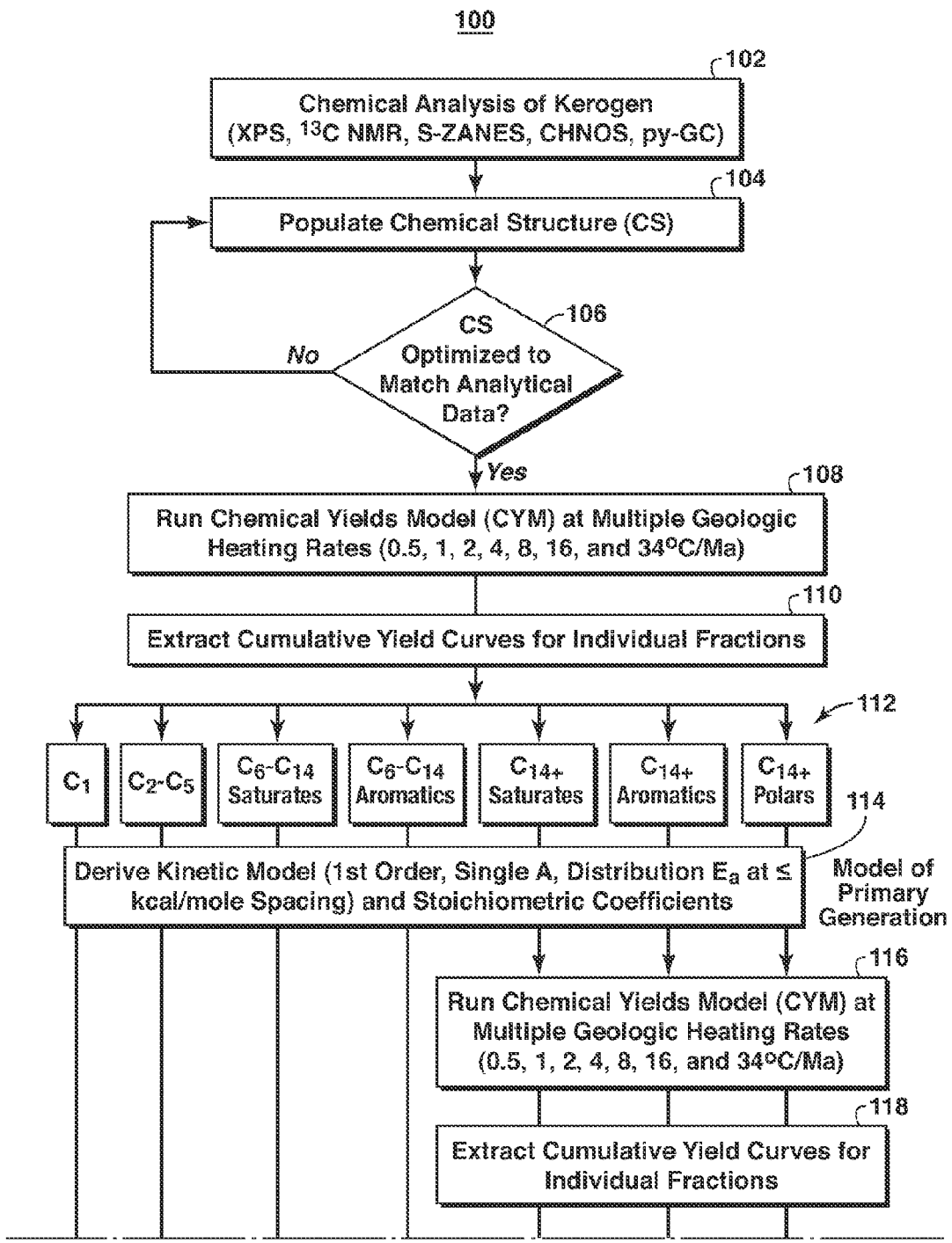
FIGS. 1A and 1B, is a process flow diagram showing a method for predicting petroleum production in accordance with an exemplary embodiment of the present invention.

In the following detailed description section, the specific embodiments of the present invention are described in connection with preferred embodiments. However, to the extent that the following description is specific to a particular embodiment or a particular use of the present invention, this is intended to be for exemplary purposes only and simply provides a description of the exemplary embodiments. Accordingly, the invention is not limited to the specific embodiments described below, but rather, it includes all alternatives, modifications, and equivalents falling within the true spirit and scope of the appended claims.

At the outset, and for ease of reference, certain terms used in this application and their meanings as used in this context are set forth. To the extent a term used herein is not defined below, it should be given the broadest definition persons in the pertinent art have given that term as reflected in at least one printed publication or issued patent.

As used herein, the term "basin model" refers to a simplification of the earth and its processes with the intent being to track the dynamic evolution of one or more of those processes through time. For example, the processes related to the generation and migration of hydrocarbons is commonly modeled with the intent to determine which of several possible structural culminations may be the most prospective for containing a commercial accumulation. Basin models use data from seismic, well control and knowledge of the geology of the area to construct a numerical model of the region and to track the changes in the various modeled parameters through time to reach a set of predictions that are then calibrated to the known information at the present. The model parameters are then adjusted within geologically reasonable bounds until a successful match and calibration is reached. Prediction can then be made at locations away from the calibration points.

As used herein, the term "kerogen" refers to a solid, carbonaceous material. When kerogen is imbedded in rock formations, the mixture is referred to as oil shale. This is true whether or not the mineral is, in fact, technically shale, that is, a rock formed from compacted clay. Kerogen is subject to decomposing upon exposure to heat over a period of time. Upon heating, kerogen molecularly decomposes to produce oil, gas, and carbonaceous coke. Small amounts of water may also be generated. The oil, gas and water fluids are mobile within the rock matrix, while the carbonaceous coke remains essentially immobile. Kerogen may be classified into four distinct groups: Type I, Type II, Type III, and Type IV. Kerogen types used herein are as defined in Tissot and Welte (Tissot, B. P. and Welte, D. H., Petroleum Formation and Occurrence, second edition, Springer-Verlag, Berlin, 1984, p. 151). The maturation sequence for kerogen that typically occurs over geological time is due to burial leading to exposure to increased temperature and pressure. Classification of kerogen type may depend upon precursor materials of the kerogen. The precursor materials transform over time into macerals or amorphous masses. Macerals are microscopic structures that have distinguishing morphologies, different chemical structures and properties depending on the precursor materials from which they are derived. Amorphous kerogens have no distinguishing morphological features that can be used to characterize its precursor materials, but may have different chemical structures and properties.

As used herein, "tangible machine-readable medium" refers to a medium that participates in directly or indirectly providing signals, instructions and/or data to a processing system. A machine-readable medium may take forms, including, but not limited to, non-volatile media (e.g., ROM, disk) and volatile media (RAM). Common forms of a machine-readable medium include, but are not limited to, a floppy disk, a flexible disk, a hard disk, a magnetic tape, other magnetic medium, a CD-ROM, other optical medium, punch cards, paper tape, other physical medium with patterns of holes, a RAM, a ROM, an EPROM, a FLASH-EPROM, or other memory chip or card, a memory stick, and other media from which a computer, a processor or other electronic device can read.

As used herein, "NSO" or "NSOs" refers to nitrogen, sulfur, and oxygen containing compounds.

Some portions of the detailed descriptions which follow are presented in terms of procedures, steps, logic blocks, processing and other symbolic representations of operations on data bits within a computer memory. These descriptions and representations are the means used by those skilled in the data processing arts to most effectively convey the substance of their work to others skilled in the art. In the present application, a procedure, step, logic block, process, or the like, is conceived to be a self-consistent sequence of steps or instructions leading to a desired result. The steps are those requiring physical manipulations of physical quantities. Usually, although not necessarily, these quantities take the form of electrical or magnetic signals capable of being stored, transferred, combined, compared, and otherwise manipulated in a computer system.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present application, discussions utilizing the terms such as "processing", "computing", "defining", "redefining", "identifying", "grouping", "preparing", "predicting", "comparing", or the like, refer to the action and processes of a computer system, or similar electronic computing device, that transforms data represented as physical (electronic) quantities within the computer system's registers and memories into other data similarly represented as physical quantities within the computer system memories or registers or other such information storage, transmission or display devices. Example methods may be better appreciated with reference to flow diagrams.

While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks. While the figures illustrate various actions occurring in serial, it is to be appreciated that various actions could occur concurrently, substantially in parallel, and/or at substantially different points in time.

A basin model according to an exemplary embodiment of the present invention comprises an interactive tool that geologists may use for a variety of purposes. For example, the model may be used to test the impact of various geologic scenarios such as source characteristics, thermal history, structural tectonics and the like on potential plays and prospects. Another use of the model may include assessing the charge risk associated with each of the various elements of a given petroleum system, such as determining if there is adequate source richness, sufficient source volume, adequate source maturity, and appropriate timing of generation relative to timing of trap formation, to name just a few examples. Another exemplary use of model includes estimating the volume of petroleum generated from a given volume of source rock(s), the volume of petroleum expelled from the source rock, the petroleum losses during migration, and ultimately the quantity of petroleum delivered to the trap(s).

Depending on the sophistication of the model (and of the data upon which the model is based), the basin model may help the geologist address issues such as the timing of hydrocarbon generation relative to the timing a trap formation. The model may also be useful in predicting the volumes of hydrocarbons delivered to a trap and the hydrocarbon type (liquid vs. gas and their relative proportions) likely to be currently present in the trap. In addition, the model may be used to predict the physical state of the hydrocarbon charge (Gas-Liquid phase behavior at specific pressure-temperature) and the composition of the gas/liquids to assess economic value. In one exemplary embodiment of the present invention, the model may assist in determining the possible migration paths to the prospect. Also, the model may be used to predict the possible post-charge loss of hydrocarbons from the trap (leakage through seal, tilt and spill of trap, thermal cracking, biodegradation and the like).

A basin model in accordance with an exemplary embodiment of the present invention may be constructed by integrating various types of geological and geochemical data. A thermal history is defined that is based on geophysical models/measurement (for example, tectonic reconstruction, basinal heat flow, well temperatures) and or geochemical measurements (for example, vitrinite reflectance data, Rock-Eval data, apatite fission track data, fluid inclusion data, oil/gas molecular and isotopic compositions or the like). The generative potential of source rock units are specified by their organic richness (for example, percentage of total organic content or % TOC, Rock-Eval HI) and their spatial distribution. A generative model (kinetics and product yields) is assigned to individual source rock units based on either direct measurement or extrapolation of organic facies. The thermal history is then applied to the kinetic model and the timing and amount of oil/gas generated is calculated over the course of the basin evolution. These calculations are then compared to models of potential migration pathways and the timing of trap and seal formation, resulting in a prediction of the petroleum accumulations.

The prediction of the amount and composition of oil and gas generated and expelled from organic rich source rocks is a key factor in basin simulations of petroleum systems. Other aspects of basin modeling, such as migration, trap formation, and seal integrity, are equally important, but are not discussed further as they are not relevant to an exemplary embodiment of the present invention. Determining the composition of oil and gas as it is expelled from the source rocks consists of modeling three major processes. The first process comprises the manner in which kerogen (the solid organic matter within source rocks that generates oil) reacts at the specified time-temperature history experienced by the source rocks over geologic time. This includes determining the rate of the reaction (kinetics) and the composition of the products (bitumen) that is formed. The second process comprises the mechanisms responsible for expelling the bitumen from the kerogen out of the source rock. Expulsion is known to be controlled by the amount and chemistry of the kerogen. Chemical fractionation occurs whereby saturated and aromatic hydrocarbons are selectively expelled while polar compounds and asphaltenes (collectively known as NSO's for compounds that contain nitrogen, sulfur, and/or oxygen) are selectively retained. The third process comprises secondary thermal cracking of the bitumen (retained within the source rock matrix) or expelled petroleum (either along migration pathways or within reservoir rocks) may occur that further alters the composition of the petroleum.

The timing of petroleum (oil and gas) generation from source rocks is dependent on the kinetic model. These kinetic models may be derived from laboratory experiments where a source rock, kerogen, asphaltene, or other carbonaceous material is artificially matured and the product yields are measured as a function of varying heating rate, temperature, and/or time. Presently, most models of oil and gas generation are based on measurements of pyrolyzate yields from experiments conducted on a specific sample that are then fitted to a series of parallel first-order reactions or other kinetic reaction schemes. As set forth above, these laboratory studies accelerate the temperature (heating rate) to compensate for short reaction time. Hence, models are derived from reactions occurring at temperatures from ~250 to 650° C. over very short time periods (typically minutes to less than 3 days) and are then extrapolated to occur at ~100 to 170° C. over millions of years. This extrapolation requires spanning rates that differ by about 14 orders of magnitude. An alternative approach to running individual source samples is to develop generic models that represent either global or basinal average kinetics for a broadly defined organic facies (for example, marine shale, terrestrial coal, and carbonate).

Those of ordinary skill in the art will recognize the importance of selecting the appropriate kinetic model. However, there is generally no consensus as to how the best kinetic model should be determined. The fact that significant differences in pyrolysate yields and modeled results emerge depending on whether the reactions are conducted under open or closed and under hydrous or anhydrous conditions has lead to an extended and unresolved discussion of the accuracy of such models when applied to geologic thermal histories and to whether the parallel reaction concept is sufficient to capture the actual nature of thermal reactions of kerogen. Indeed, reactions are known to occur under high temperature laboratory conditions that are not the same as those that occur in sedimentary basins at lower temperatures over much greater time. Furthermore, some cases studies have shown empirically that laboratory-based kinetic models of kerogen decomposition must be artificially adjusted to confirm to observations.

With respect to petroleum composition, kinetic models based on bulk kerogen thermal decomposition can only approximate actual product yields and do not model product composition. In a product generation approach, a separate kinetic model may be determined for each product lump that may have different frequency factors. As used herein, the term "product lump" means a group of reaction products that are similar in chemical composition and behavior. A method in accordance with an exemplary embodiment of the present invention may desirably be performed such that the individual products are quantified as a function of time/temperature and may involve complex analyses of closed-system pyrolysates or customized instrumentation. In the kerogen degradation approach, where a discrete distribution of activation energies ($E_a$) usually with a fixed frequency factor (A) is determined for the bulk kerogen, each individual activation energy is divided into portions representative of the lumped components. This approach is considered easier to define as the bulk kerogen decomposition kinetics can be determined by routine open-system pyrolysis methods and the products can be independently quantified.

With respect to petroleum expulsion, it is typical for the majority of the products formed in the laboratory heating experiments to be polar (NSO-containing) compounds rather than saturated and aromatic hydrocarbons that dominate expelled petroleum. Research and field observation has shown that the bitumen retained in a source rock is enriched in polar compounds (NSOs and asphaltenes) while the expelled petroleum is enriched in hydrocarbons. Depending on the expulsion model, the compositional model may reflect either primary bitumen or expelled petroleum. A bitumen model may desirably calculate the chemical fractionation that occurs upon expulsion, while a petroleum model has already adjusted the lumped component compositions to reflect this fractionation.

After petroleum has been expelled, it may undergo secondary thermal cracking reactions that further alter its composition. This secondary cracking may occur within the source rock mineral matrix, along migration pathways, or within reservoir rocks. Beyond simple Oil→Gas models, an exemplary embodiment of the present invention models compositional changes in petroleum resulting from secondary cracking.

Figures 1, 1A, 1B:
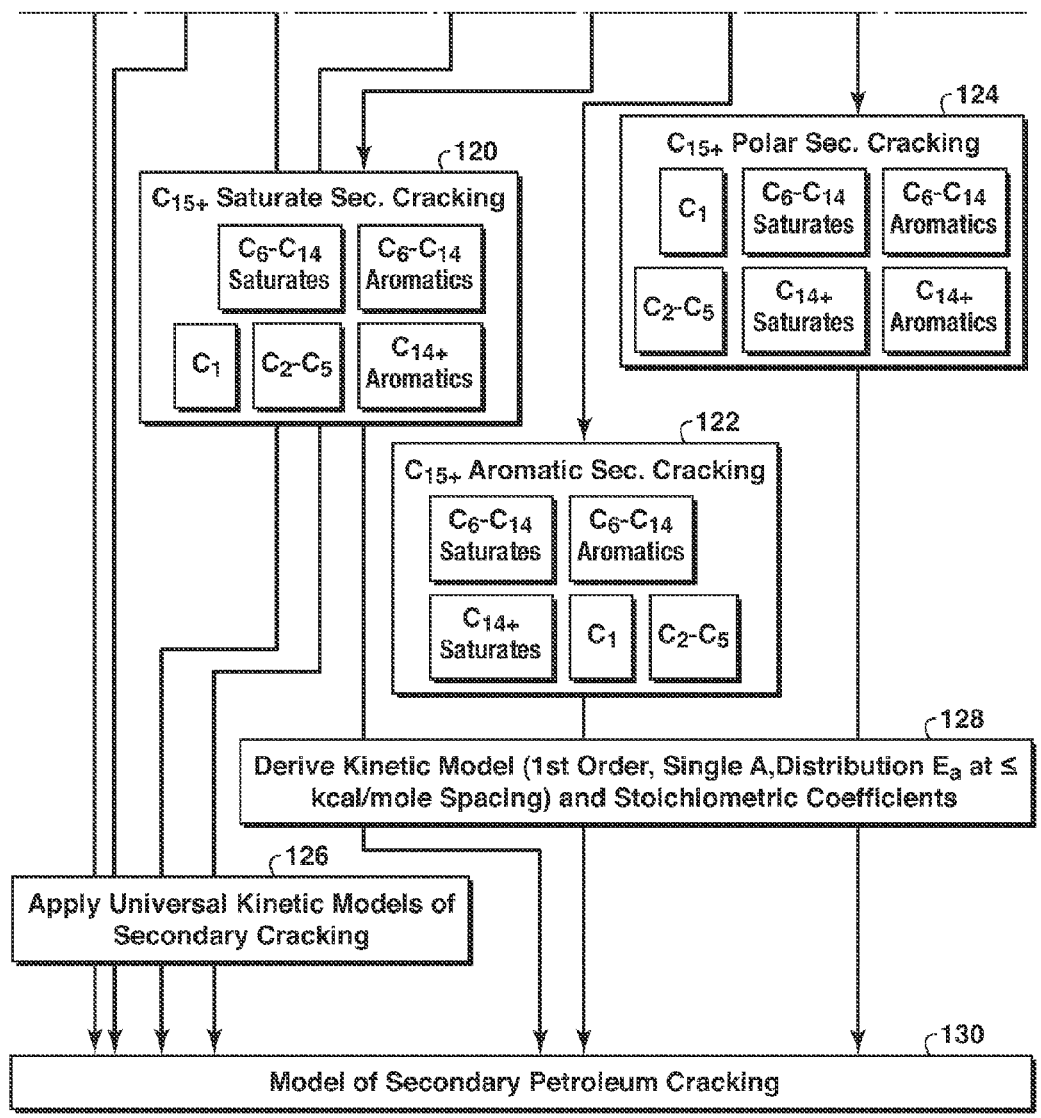
FIG. 1, which includes

FIG. 1, which includes FIG. 1A and 1B, is a process flow diagram showing a method for predicting differences in subsurface conditions in accordance with an exemplary embodiment of the present invention. The method is generally referred to by the reference number 100. At block 102, a chemical analysis of a kerogen is performed. At block 104, a chemical structure, referred to as CS in FIG. 1, is populated. A decision is made regarding whether the chemical structure has been optimized to match known analytical data, as shown at block 106. If the chemical structure is not optimized with respect to known analytical data, process flow returns to block 104, where the chemical structure is re-populated.

At block 108, modeling of the amount and composition of generated and expelled oil and gas is performed on the chemical structure using a process known as chemical structure-chemical yields modeling or CY-CSM. One example of a CS-CYM is generally described in U.S. Pat. No. 7,344,889, entitled "Chemical Structural and Compositional Yields Model for Predicting Hydrocarbon Thermolysis Products", which issued to Kelemen, et al. on Mar. 18, 2008. A CY-CSM is also described in the following publication: Freund H., Walters, C. C. Kelemen S. R., Siskin M., Gorboty, M. L., Curry D. J., Bence A. E., 2006. Organic Geochemistry, 38 288-305. Predicting Oil and Gas Compositional Yields via Chemical Structure-Chemical Yield Modeling (CS-CYM): Part 1—Concepts and Implementation. Another example of a CY-CSM is set forth in U.S. Patent Application Publication No. 2010/0161302 entitled "Method for Predicting Petroleum Expulsion", by Walters, et al.

In an exemplary embodiment of the present invention, CY-CSM relies on constructing a representative model of the molecular structure of a kerogen using constraints from numerous chemical analyses, modeling the thermal reactions that occur within this representative structure, and applying a thermodynamic-based theory of expulsion and chemical fractionation to calculate the product yields. This model has been shown to predict the yields and composition of oil and gas generated in high temperature experiments. When basinal heating rates are used, the compositions of both expelled oil and retained bitumen are modeled following the reaction pathways, kinetics, and expulsion mechanisms that occur under these conditions and are not extrapolations of high-temperature experimental data. Yield curves for individual fractions are extracted, as shown at block 110 of FIG. 1A. For example, yield curves for a group of hydrocarbons 112 may be individually extracted, as set forth below.

In performing CY-CSM in accordance with an exemplary embodiment of the present invention, by providing the amount and kinetic model for individual hydrocarbons (for example, $C_1$, $C_2$, $C_3$, $C_4$, and $C_5$ hydrocarbons) or lumped hydrocarbons (for example, $C_6$-$C_{14}$ Aromatics, $C_6$-$C_{15}$ Saturates, $C_{15+}$ Saturates, $C_{15+}$ Aromatics, and $C_{15+}$ polars). A kinetic model for each of the group of hydrocarbons 112 is produced, as shown at block 114. Because the kinetics of each expelled product are modeled using the yields calculated from a coupled generation and expulsion model, each product may be considered independently within the basin simulator. Hence, instead of using a kerogen decomposition kinetic model where the stoichiometric yields for each activation energy bin may vary, a kinetic model for each compositional component is defined. As such, the implementation is extremely flexible as new components (for example, non-HC gases) or refinements of a lumped component (for example, $C_{15+}$ polars modeled as $C_{15+}$ resins and $C_{15+}$ asphaltenes) can be easily changed without affecting the other component models. The kinetics of the individual components are determined by running CS-CYM at varying heating rates typical of geologic basins (0.5 to 32° C./million years (Ma) are given as examples in block 108) and fitting the calculated yield curves to a discrete activation energy model.

In the exemplary embodiment shown in FIG. 1A, additional CS-CYM modeling is performed on a subset of the group of hydrocarbons 112, as shown at block 116. Yield curves for the subset of the group of hydrocarbons are extracted for the resulting individual fractions, as shown at block 118. Examples of these individual fractions include a first fraction 120, a second fraction 122 and a third fraction 124. As shown in FIG. 1B, the first fraction 120 includes input from additional ones of the group of hydrocarbons 112. At block 126, kinetic models of secondary cracking are applied to a second subset of the group of hydrocarbons 112. At block 128, kinetic models and stoichiometric coefficients are derived based on input data from the first fraction 120, the second fraction 122 and the third fraction 124.

As shown at block 130, modeling of secondary cracking reactions, which further alter expelled oil composition via thermal reactions that occur within source rock mineral matrices, along migration pathways, and within reservoir rock, also are calculated using CS-CYM. Here, the generation/expulsion of a compositional lump (for example, $C_{15+}$ Saturates) is first modeled as described above, and the individual product is trapped. The trapped product is then re-run within CS-CYM under closed conditions and the product yields are calculated.

Figure 2:
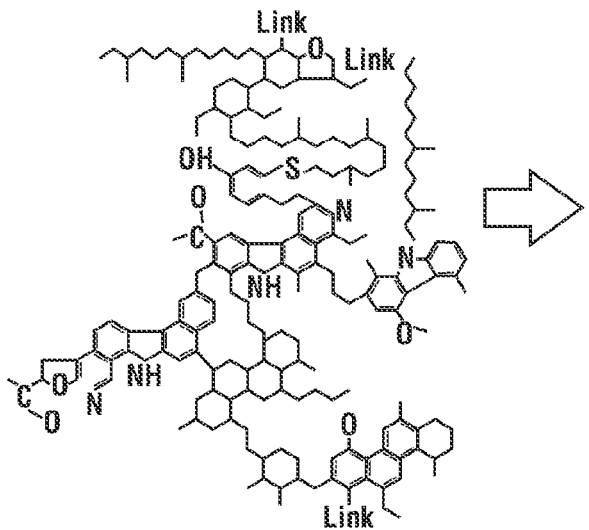
FIG. 2 is a diagram that shows the modeling of expelled petroleum in accordance with an exemplary embodiment of the present invention.
Figure 2:
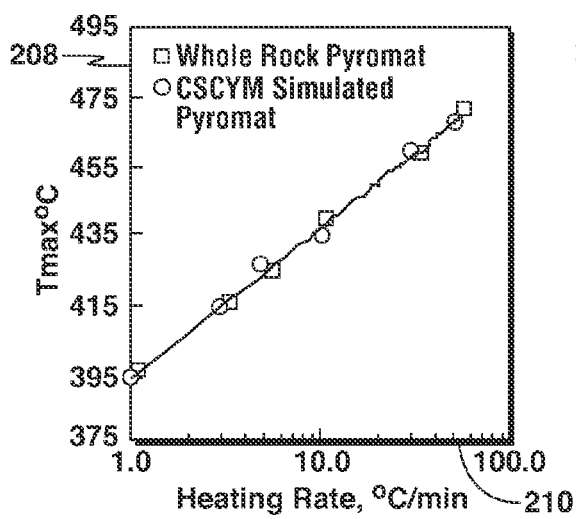
Figure 2:
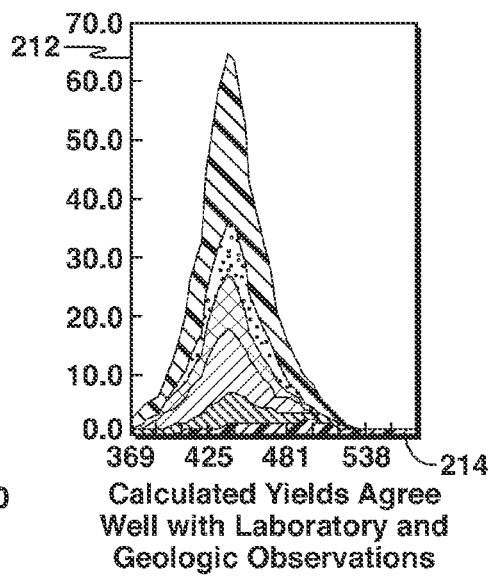

FIG. 2 is a diagram that shows the modeling of expelled petroleum in accordance with an exemplary embodiment of the present invention. The diagram is generally referred to by the reference number 200. In an exemplary embodiment of the present invention, CS-CYM is used to derive the data needed to determine the yields and kinetic model for the coupled generation/expulsion of individual lumped products and the yields and secondary cracking kinetics of the $C_{14+}$ lumped products.

A first panel 202 of the diagram 200 shows a snapshot of a Type 1 kerogen substructure. To create this snapshot, kerogen is isolated from its rock matrix and analyzed using numerous analytical methods (for example, elemental CHNOS analysis, solid-state $^{13}$C NMR, X-ray photoelectron spectroscopy, Sulfur-XANES, pyrolysis-GC or the like) that provide constraining input values used to construct a representation (~1 million atoms) of the kerogen structure. The chemical structure of the kerogen is then placed within a reaction network that predicts the composition of the generated and expelled products under specified temperature conditions, as shown at a second panel 204 of the diagram 200. For simulating high temperature, open system experiments such as those typically used for determining bulk kerogen degradation kinetics, CS-CYM first calculates the products produced from kerogen cracking and then determines if the product is sufficiently volatile to be considered as an expelled product. Yield curves for expelled products may be compared to known geologic data, as shown in a third panel 206 of the diagram 200. The third panel 206 includes a left graph and a right graph. The left graph includes a y-axis 208 that represents a maximum temperature in degrees Celsius. An x-axis 210 of the left graph represents a heating rate in degrees Celsius per minute. The right graph of the third panel 206 includes a y-axis 212 that represents the rate of expelled products from a simulation of an open-system laboratory pyrolysis in units of mg expelled product/g total carbon/0.2 minutes. An x-axis 214 of the right graph represents temperature in units of degrees Celsius. The calculated yields compare very well with laboratory yields when kerogens are reacted at high temperatures and heating rates, suggesting that the reaction network is replicating the basic chemical reaction and expulsion processes that occur under these conditions.

With respect to identifying the constituent products as shown in the second panel of the diagram 204, the products replicate high temperature laboratory results. A CS-CYM program is used to determine the product yield under geologic heating rates. The generated products are calculated as several thousand individual species, then lumped into chemical classes defined as: $C_1$, $C_2$-$C_5$, $C_6$-$C_{14}$ saturates, $C_6$-$C_{14}$ aromatics+polars, $C_{15+}$ saturates, $C_{15+}$ aromatics, $C_{15+}$ polars. The $C_2$-$C_5$ component may be further divided into $C_2$, $C_3$, $C_4$, $C_5$ hydrocarbons if the final model is to be used in an Equation of State (EOS) calculation to determine phase behavior. $C_{15+}$ polars may be split into $C_{15+}$ NSO and $C_{15+}$ asphaltenes based on a solubility test of individual components.

As shown in the second panel 204, the composition of the expelled products are calculated using a simplified formulation of a thermodynamic theory of expulsion and chemical fractionation that is an extended Flory-Rehner Regular Solution. This expulsion theory couples concepts of polymer theory to describe the amount of bitumen that can dissolve in a kerogen matrix with Regular Solution theory that explains which molecules are preferentially retained and which are expelled. A simplification of the theory is desirable as an exact calculation of the composition of the equilibrated retained and expelled is too currently computationally intensive to be run for all components at all time steps.

Figure 3:
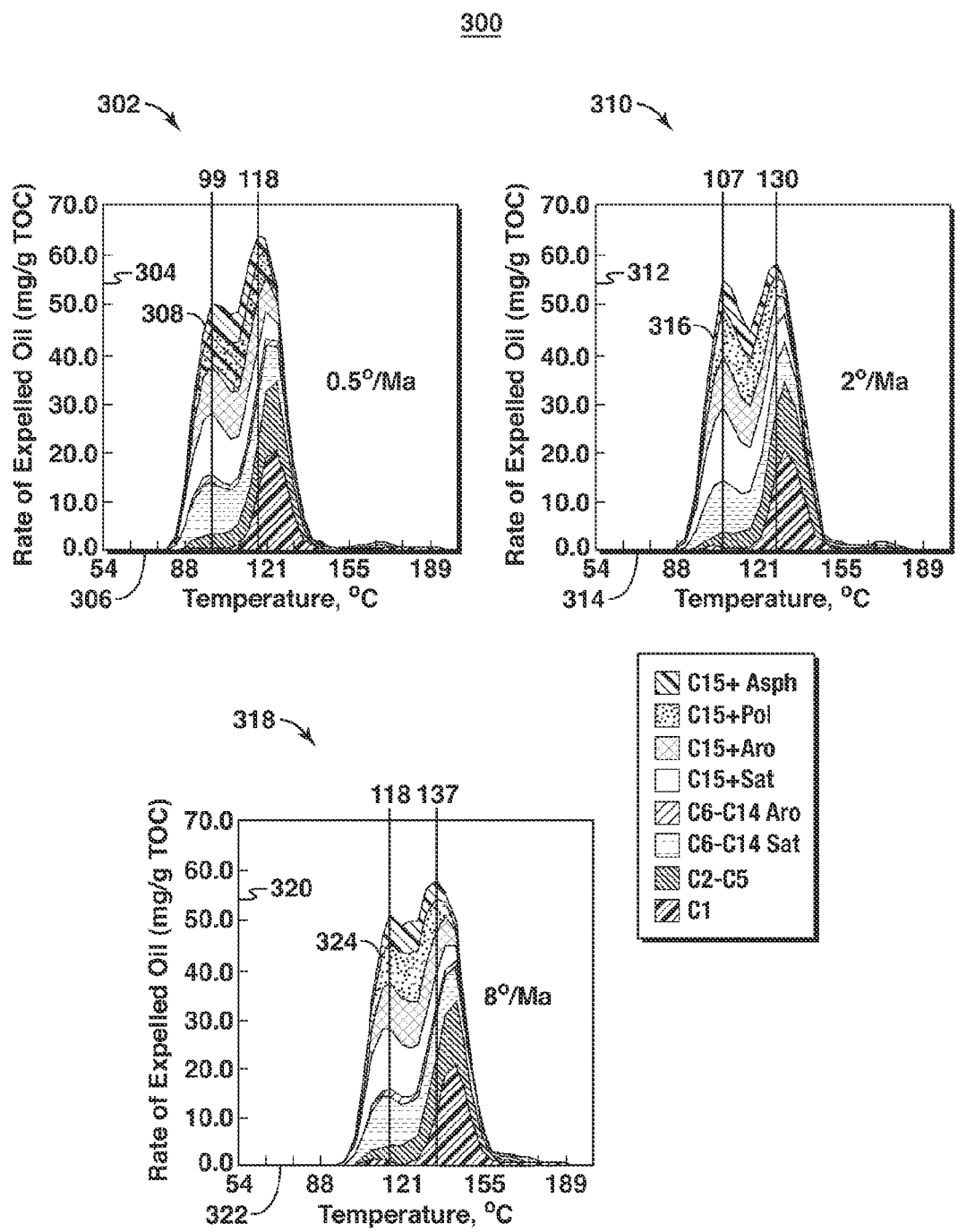
FIG. 3 is a plurality of graphs showing rate curves indicating rates of expulsion of petroleum at different heat rates.

FIG. 3 is a plurality of graphs showing rate curves indicating rates of expulsion of petroleum at different heat rates. The plurality of graphs is generally referred to by the reference number 300. For a given kerogen, the expelled products are modeled at varying heating rates. Typical heating rates used are 0.5, 1, 2, 4, 8, 16, and 32° C./Ma, which span the conditions most commonly seen in nature. In the exemplary plurality of graphs 300, a family of curves is shown for heat rates of 0.5° C./Ma, 2° C./Ma and 8° C./Ma. In particular, a first graph 302 comprises a y-axis 304 that corresponds to a rate if expelled oil at a heating rate of 0.5° C./Ma. The first graph 302 includes an x-axis 306 that corresponds to temperature in degrees Celsius. A family of curves 308 shows the rate of expelled oil for a plurality of different reaction products. Moreover, each curve within the family of curves 308 corresponds to a different reaction product.

A second graph 310 comprises a y-axis 312 that corresponds to a rate if expelled oil at a heating rate of 2° C./Ma. The second graph 310 includes an x-axis 314 that corresponds to temperature in degrees Celsius. A family of curves 316 shows the rate of expelled oil for a plurality of different reaction products. Moreover, each curve within the family of curves 316 corresponds to a different reaction product.

A third graph 318 comprises a y-axis 320 that corresponds to a rate if expelled oil at a heating rate of 8° C./Ma. The second graph 318 includes an x-axis 322 that corresponds to temperature in degrees Celsius. A family of curves 324 shows the rate of expelled oil for a plurality of different reaction products. Moreover, each curve within the family of curves 324 corresponds to a different reaction product.

Figure 4:
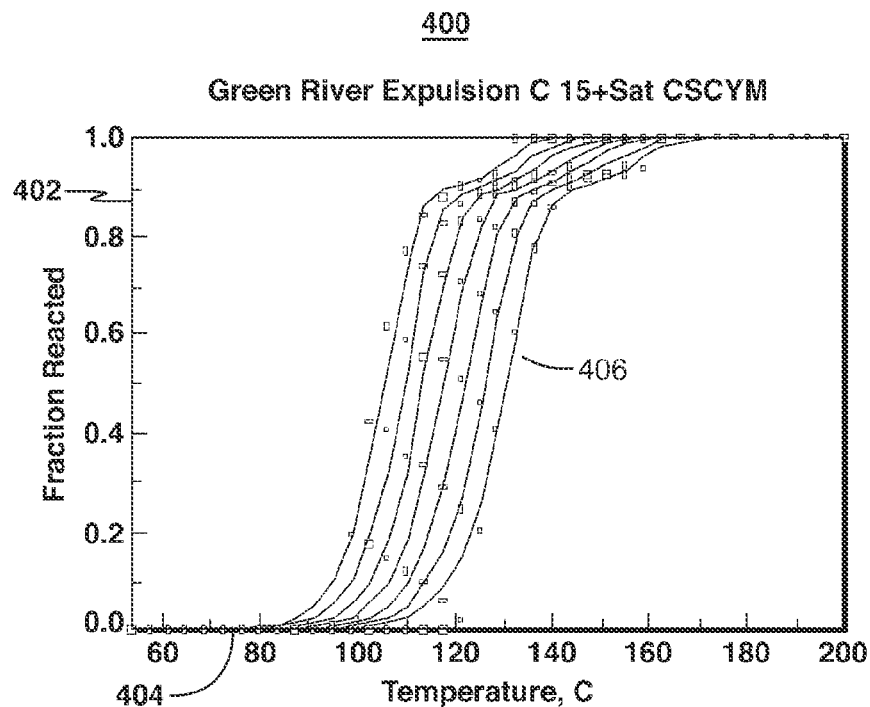
FIG. 4 is a graph showing a family of curves corresponding to cumulative yields for a particular fraction as a function of temperature at varying heating rates in accordance with an exemplary embodiment of the present invention.

FIG. 4 is a graph showing a family of curves corresponding to cumulative yields for a particular fraction as a function of temperature at varying heating rates in accordance with an exemplary embodiment of the present invention. In an exemplary embodiment of the present invention, each individual fraction or product lump is analyzed as a separate entity. The graph is generally referred to by the reference number 400. The graph 400 includes a y-axis 402 that corresponds to a fraction reacted index ranging from 0.0 to 1.0. An x-axis 404 corresponds to temperature in degrees Celsius. A family of evolution curves 406 represent cumulative yields as a function of temperature at varying heating rates. The family of evolution curves may be fitted using fitting software. From this analysis, a kinetic model is generated whereby the rate of expulsion of a specific product lump is expressed by a single frequency factor and a discrete spectrum of activation energies.

Figure 5:
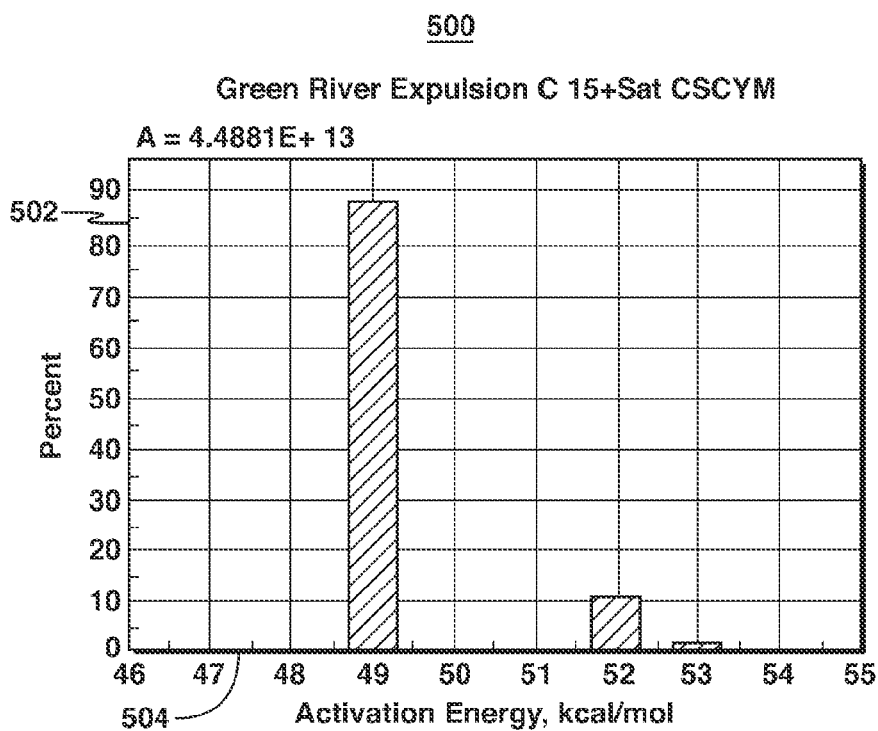
FIG. 5 is a graph showing a rate of expulsion expressed as a single frequency factor and a discrete spectrum of activation energies in accordance with an exemplary embodiment of the present invention.

FIG. 5 is a graph showing a rate of expulsion expressed as a single frequency factor and a discrete spectrum of activation energies in accordance with an exemplary embodiment of the present invention. The graph is generally referred to by the reference number 500. The graph 500 includes a y-axis 502 corresponding to a percentage rate of expulsion of a particular fraction. An x-axis 504 corresponds to activation energy in units of kcal/mol. Thus, the bars on the graph represent a percentage of overall rate of expulsion for a typical reaction product across a spectrum of activation energies.

Once the kinetics of all compositional lumps are determined, the model is completed by determining the stoichiometric coefficients for the finally cumulative product. The amount of each lumped expelled product i that is expelled from a source kerogen is calculated as: TOC×HI×$f_i$×$a_i$, where $a_i$ is a fixed coefficient. Since the kinetics of expulsion of $C_2$-$C_5$ are nearly identical, they can be calculated as a single $C_2$-$C_5$ lump. The individual $C_2$, $C_3$, $C_4$, and $C_5$ components are then separated from a fixed stoichiometric relationship ($b_i$). The residual kerogen, termed coke, is a non-mobile product that can convert to inert char and $CH_4$ at higher temperatures. The amount of coke is calculated by grams of kerogen×$f_i$×$a_{coke}$ where $a_{coke}$ is a fixed coefficient.

An example of a complete compositional yields model for expelled product is shown below in Table 1:

TABLE 1

Kinetic Models Type I (based on Green River Shale) Expelled Products and Coke

| | \multicolumn{8}{c}{Fraction} | | | | | | | |
|---|---|---|---|---|---|---|---|---|
| | C1 | C2-C5 | C6-C14Sat | C6-C14Aro | C15+ Sat | C15+ Aro | Polars | Coke |
| | | | | A, sec-1 | | | | |
| Kcal/mol | 5.44E+11 | 1.12E+14 | 3.40E+13 | 2.16E+13 | 4.49E+13 | 1.22E+13 | 3.52E+16 | 4.41E+13 |
| 47 | 0 | 0 | 0 | 0 | 0 | 0 | 0 | 0 |
| 48 | 0 | 0 | 0 | 0 | 0 | 0 | 0 | 0 |
| 49 | 0 | 0 | 0 | 13.9 | 0 | 81.44 | 0 | 0 |
| 50 | 100 | 0 | 87.93 | 10.02 | 87.93 | 1.34 | 0 | 75.86 |
| 51 | 0 | 46.02 | 0 | 0 | 0 | 15.05 | 0 | 0 |
| 52 | 0 | 5.06 | 0 | 0 | 0 | 0 | 0 | 0 |
| 53 | 0 | 0 | 10.24 | 53.33 | 10.24 | 2.16 | 0 | 17.53 |
| 54 | 0 | 48.91 | 1.83 | 9.86 | 1.83 | 0 | 50 | 6.43 |
| 55 | 0 | 0 | 0 | 8.14 | 0 | 0 | 50 | 0 |
| 56 | 0 | 0 | 0 | 4.76 | 0 | 0 | 0 | 0 |
| 57 | 0 | 0 | 0 | 0 | 0 | 0 | 0 | 0 |
| 58 | 0 | 0 | 0 | 0 | 0 | 0 | 0 | 0 |
| 59 | 0 | 0 | 0 | 0 | 0 | 0 | 0 | 0.18 |

Stoichiometric yield coefficients are shown below in Table 2.

TABLE 2

Stoichiometric Yield Coefficients

| | C1 | C2-C5 | C6-C14Sat | C6-C14Aro | C15+ Sat | C15+ Aro | Polars |
|---|---|---|---|---|---|---|---|
| $a_i$ | 0.051408 | 0.073439 | 0.183599 | 0.033048 | 0.501836 | 0.107711 | 0.04896 |

Secondary coefficients for the $C_2$-$C_5$ product lump are shown below in Table 3.

TABLE 3

% C2-C5. Fraction of individual HC's

| | C2 | C3 | C4 | C5 |
|---|---|---|---|---|
| $b_i$ | 0.15 | 0.25 | 0.3 | 0.3 |

Coefficients for coke are shown below in Table 4.

TABLE 4

Coke

| | C1 |
|---|---|
| $a_{coke}$ | 0.253051 |

Coefficients relating to coke formation are shown below in Table 5.

TABLE 5

Coke Formation

Coke ⇒ 0.069358$C_1$ + 0.920642Char
A = 6 × $10^{13}$ $Ma^{-1}$

| Ea | fraction |
|---|---|
| 60 | 0.31 |
| 62 | 0.26 |
| 64 | 0.17 |
| 66 | 0.13 |

TABLE 5-continued

Coke Formation

| 68 | 0.09 |
| 70 | 0.04 |

The discrete energy kinetic models for expelled products are readily incorporated into basin simulators as the form is similar to what is currently used for kerogen degradation kinetics. In accordance with an exemplary embodiment of the present invention, the models are for expelled product. Hence, the generation and expulsion mechanisms, along with chemical fractionation, are inherently built into the model and the simulator need not calculate generation and expulsion using different models and/or principles.

Secondary cracking occurs after petroleum has migrated out of the source kerogen. These cracking reactions may occur to bitumen trapped in pore spaces within the source rock matrix, along migration pathways, and in reservoir rocks. Thermal cracking can significantly alter the composition of petroleum.

Figure 6:
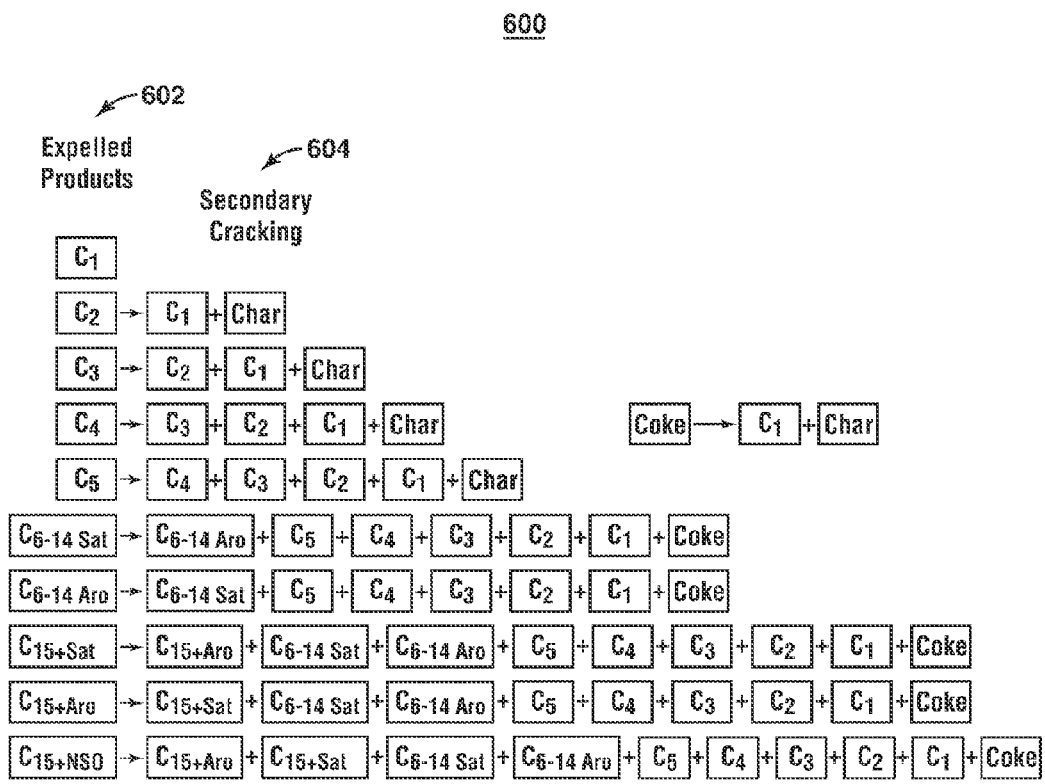
FIG. 6 is a diagram showing an outline of secondary cracking reactions in accordance with an exemplary embodiment of the present invention.

FIG. 6 is a diagram showing an outline of secondary cracking reactions in accordance with an exemplary embodiment of the present invention. The diagram is generally referred to by the reference number 600. The diagram shows a vertical column of expelled products 602 and a corresponding series of secondary cracking reaction products 604.

To model the secondary cracking reactions, CS-CYM may be performed in a manner that the expelled products for each chemical lump were mathematically trapped as they were expelled. These molecular pools were then subjected to a second round of heating at various heating rates under closed-system conditions and the degradation of each product lump calculated. From these rates curves, a kinetic model was fashioned in the same manner as described above. This procedure was applied to the $C_{15+}$ fractions. While the models for the thermal cracking of $C_{15+}$ saturated and aromatic hydrocarbons were similar regardless of the composition of the original source kerogen, the thermal cracking of the $C_{15+}$ polar compounds differ. Consequently, the origin of the polar compounds must be tracked within the basin simulator. The kinetics for the thermal cracking of $<C_{15+}$ fractions were derived from literature values and laboratory heating experiments.

Figure 7:
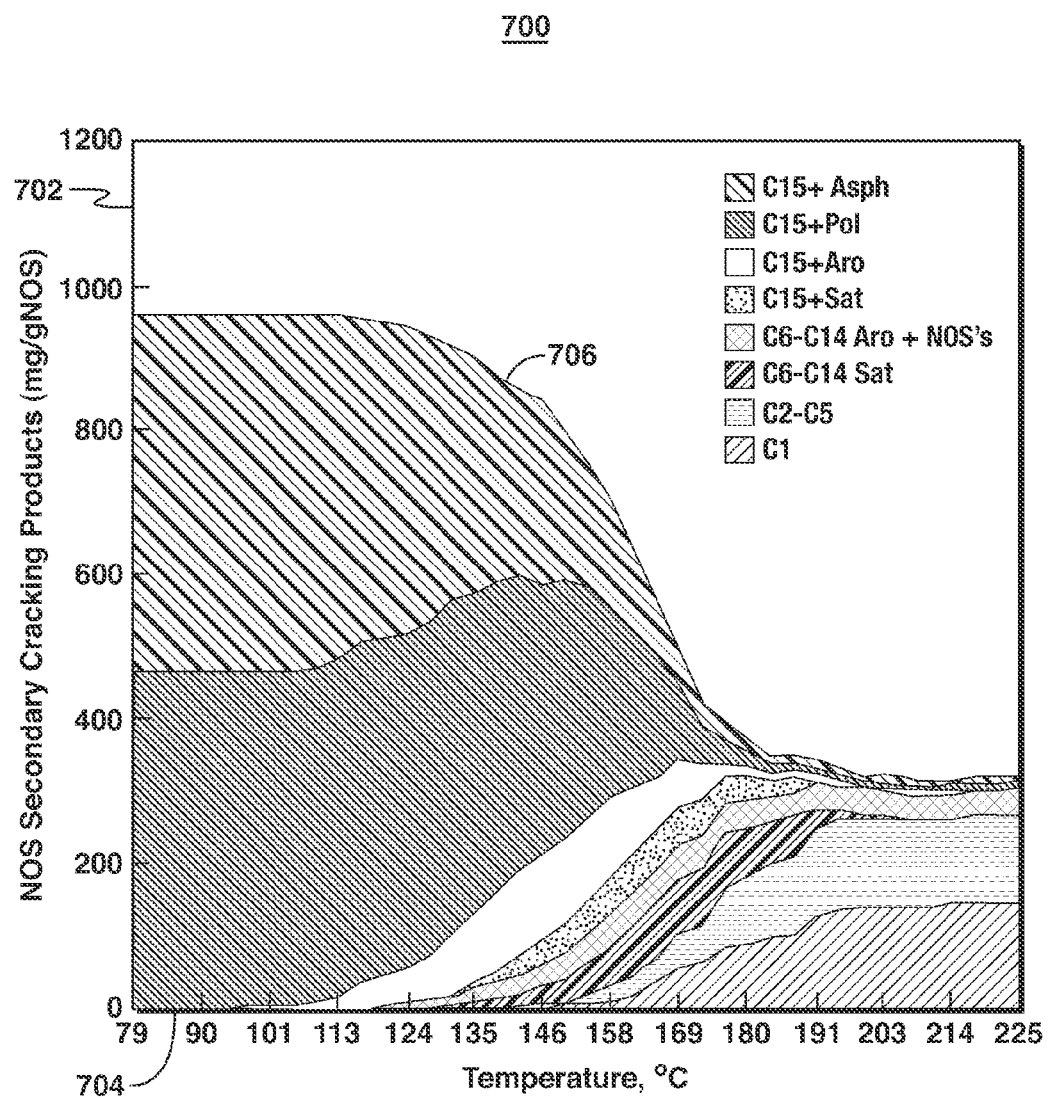
FIG. 7 is a graph showing an output from a calculation of the thermal cracking of a Polars (NSO) fraction in accordance with an exemplary embodiment of the present invention.

FIG. 7 is a graph showing an output of mobile products from a calculation of the thermal cracking of a Polars (NSO) fraction in accordance with an exemplary embodiment of the present invention. The graph is generally referred to by the reference number 700. The Polars (NSO) fraction shown in FIG. 7 is from Green River Shale (Type I) kerogen at a 0.5° C./Ma heating rate.

The graph 700 comprises a y-axis 702 that corresponds to NSO secondary cracking products measured in mg/gNSO. An x-axis 704 corresponds to temperature in degrees Celsius. Each of a family of curves 706 corresponds to a different component of the Polars (NSO) fraction.

Figure 8:
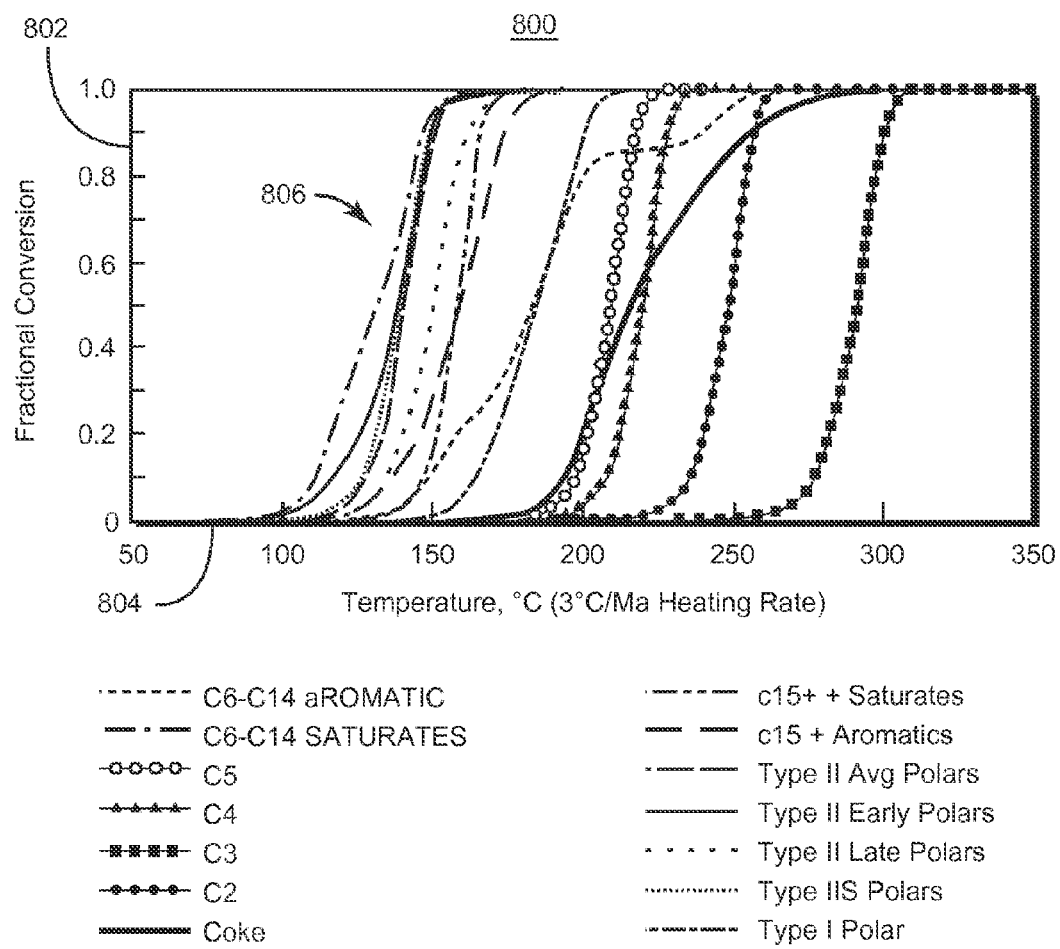
FIG. 8 is a graph showing a comparison of overall thermal cracking expressions in accordance with an exemplary embodiment of the present invention.

FIG. 8 is a graph showing a comparison of overall thermal cracking expressions in accordance with an exemplary embodiment of the present invention. The graph is generally referred to by the reference number 800. The graph 800 comprises a y-axis 802 corresponding to a percentage of fractional conversion ranging from 0 to 1. An x-axis 804 corresponds to temperature in degrees Celsius. Each of a family of curves 806 corresponds to a different component of a fraction.

Figure 9:
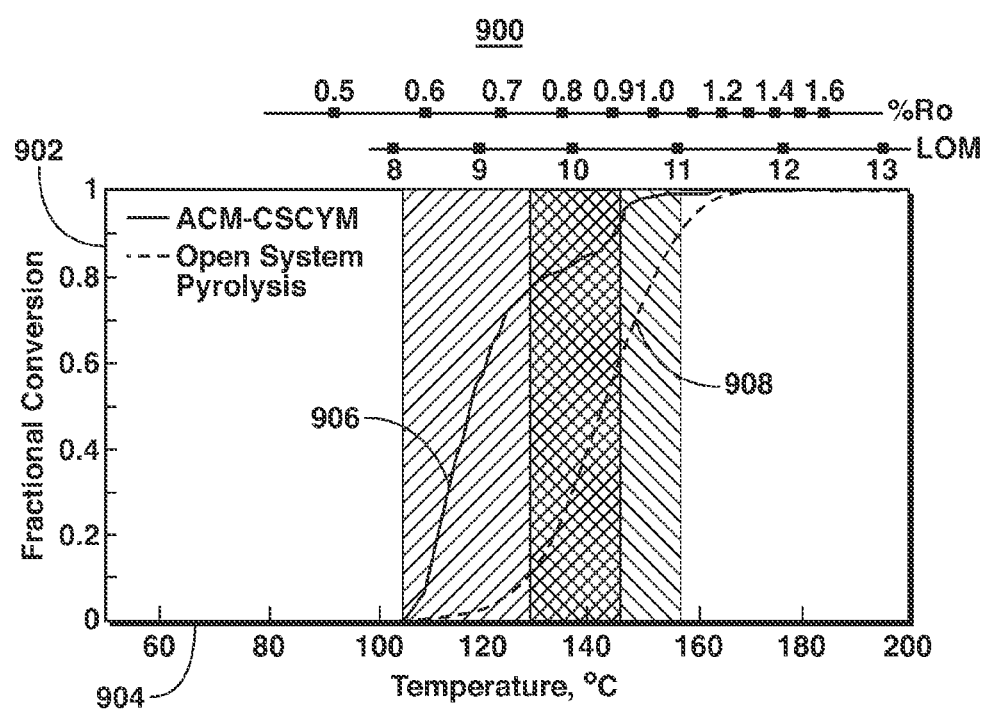
FIG. 9 is a graph showing a comparison between results produced by an open system pyrolysis approach and an exemplary embodiment of the present invention.

FIG. 9 is a graph showing a comparison between results produced by an open system pyrolysis approach and an exemplary embodiment of the present invention. The graph is generally referred to by the reference number 900. The graph 900 comprises a y-axis 902 corresponding to a percentage of fractional conversion ranging from 0 to 1. An x-axis 904 corresponds to temperature in degrees Celsius. A first curve 906 shows results produced by an exemplary embodiment of the present invention. A second curve 908 shows results produced using an open system pyrolysis approach.

An exemplary embodiment of the present invention provides solutions that differ from known published or commercial products. For instance, in the example provided above for Type I kerogen, an exemplary embodiment of the present invention yields hydrocarbons at substantially lower temperatures than a conventional model derived from open-system pyrolysis ($A=7.86\times10^{13}$ sec$^{-1}$, $E_{mean}$=53 kcal/mol, std. dev.=1 kcal/mol) at a 4° C./Ma heating rate. Moreover, an exemplary embodiment of the present invention predicts petroleum is generated and expelled from a vitrinite reflectance of ~0.55% to ~0.95% (LOM 8 to 10.5) with a 50% fractional conversion at ~0.67%. The open-system pyrolysis kinetic model predicts petroleum is generated from ~0.7% to ~1.2% (LOM 9 to 11). The calculations were conducted using a 4° C./Ma heating rate that approximates the geothermal history of the Uinta Basin during Paleocene-Eocene subsidence.

Figure 10:
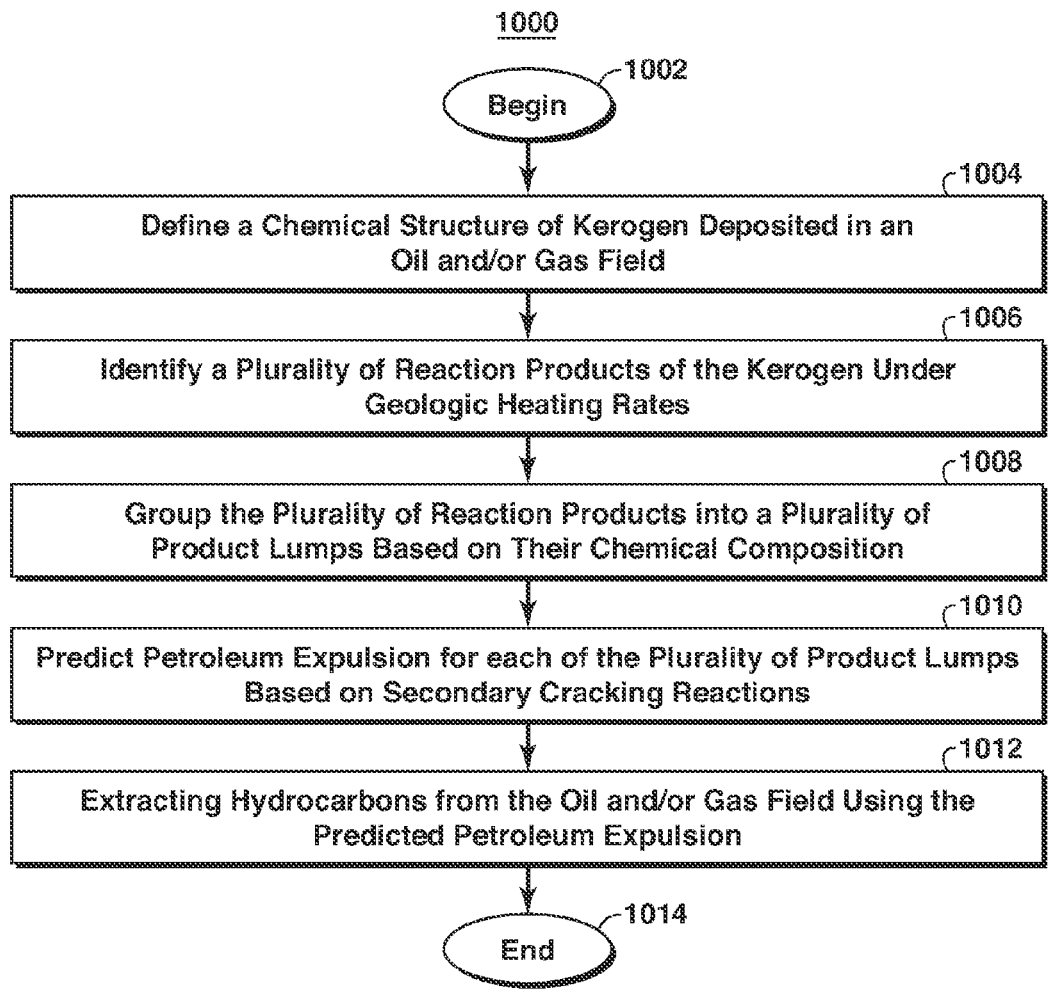
FIG. 10 is a process flow diagram showing a method for producing hydrocarbons in accordance with an exemplary embodiment of the present invention.

FIG. 10 is a process flow diagram showing a method for producing hydrocarbons in accordance with an exemplary embodiment of the present invention. The method is generally represented by the reference number 1000. At block 1002, the method begins.

A chemical structure of a kerogen deposited in the oil and/or gas field is defined, as shown at block 1004. At block 1006, a plurality of reaction products of the kerogen under geologic heating rates is identified. The reaction products are grouped into a plurality of product lumps based on their chemical composition, as shown at block 1008. At block 1010, petroleum expulsion for each of the plurality of product lumps is predicted based on secondary cracking reactions. Hydrocarbons are extracted from the oil and/or gas field using the predicted petroleum expulsion, as shown at block 1012. At block 1014, the process ends.

Figure 11:
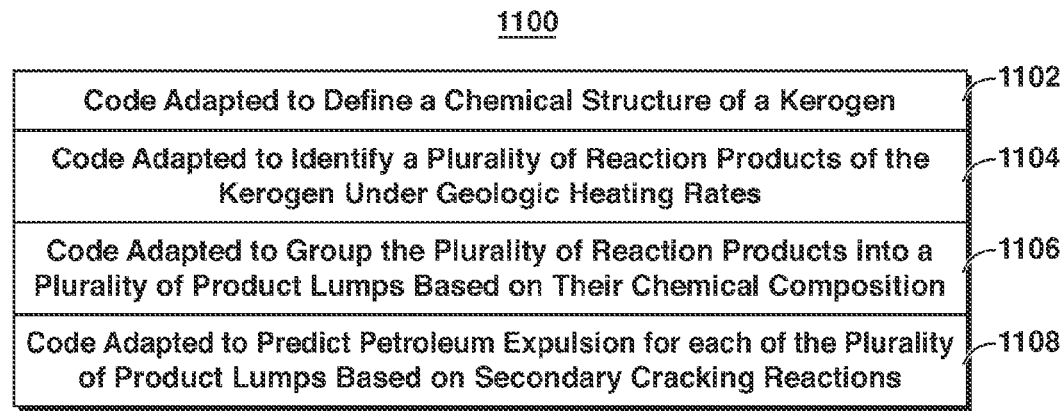
FIG. 11 is a diagram of a tangible, machine-readable medium in accordance with an exemplary embodiment of the present invention.

FIG. 11 is a diagram of a tangible, machine-readable medium in accordance with an exemplary embodiment of the present invention. The tangible, machine-readable medium is generally referred to by the reference number 1100. The tangible, machine-readable medium 1100 may comprise a disk drive such as a magnetic or optical disk or the like. In an exemplary embodiment of the present invention, the tangible, machine-readable medium 1100 comprises code 1102 adapted to define a chemical structure of a kerogen. Code 1104 adapted to identify a plurality of reaction products of the kerogen under geologic heating rates is stored on the tangible, machine-readable medium. In addition, code 1106 adapted to group the plurality of reaction products into a plurality of product lumps based on their chemical composition is stored on the tangible, machine-readable medium. Finally, the tangible, machine-readable medium stores code 1108 adapted to predict petroleum expulsion for each of the plurality of product lumps based on secondary cracking reactions.

An exemplary embodiment of the present invention relates to a method for calculating the generation and expulsion of oil and gas and its secondary thermal cracking that differs from previously published techniques. According to an exemplary embodiment of the present invention, determination of the quantity and timing of petroleum generation is performed according to a theoretical model as opposed to extrapolation of laboratory experiments. In addition, the generation and expulsion models are coupled into a single model for expelled petroleum. A theoretical model to describe the quantity and timing of generation of hydrocarbons from the secondary cracking of hydrocarbons and polar compounds may additionally be employed.

An exemplary embodiment of the present invention provides an approximation of an expulsion model for chemical fractionation. In addition, the stoichiometry and kinetics of the secondary cracking of individual lumps are modeled.

Figure 12:
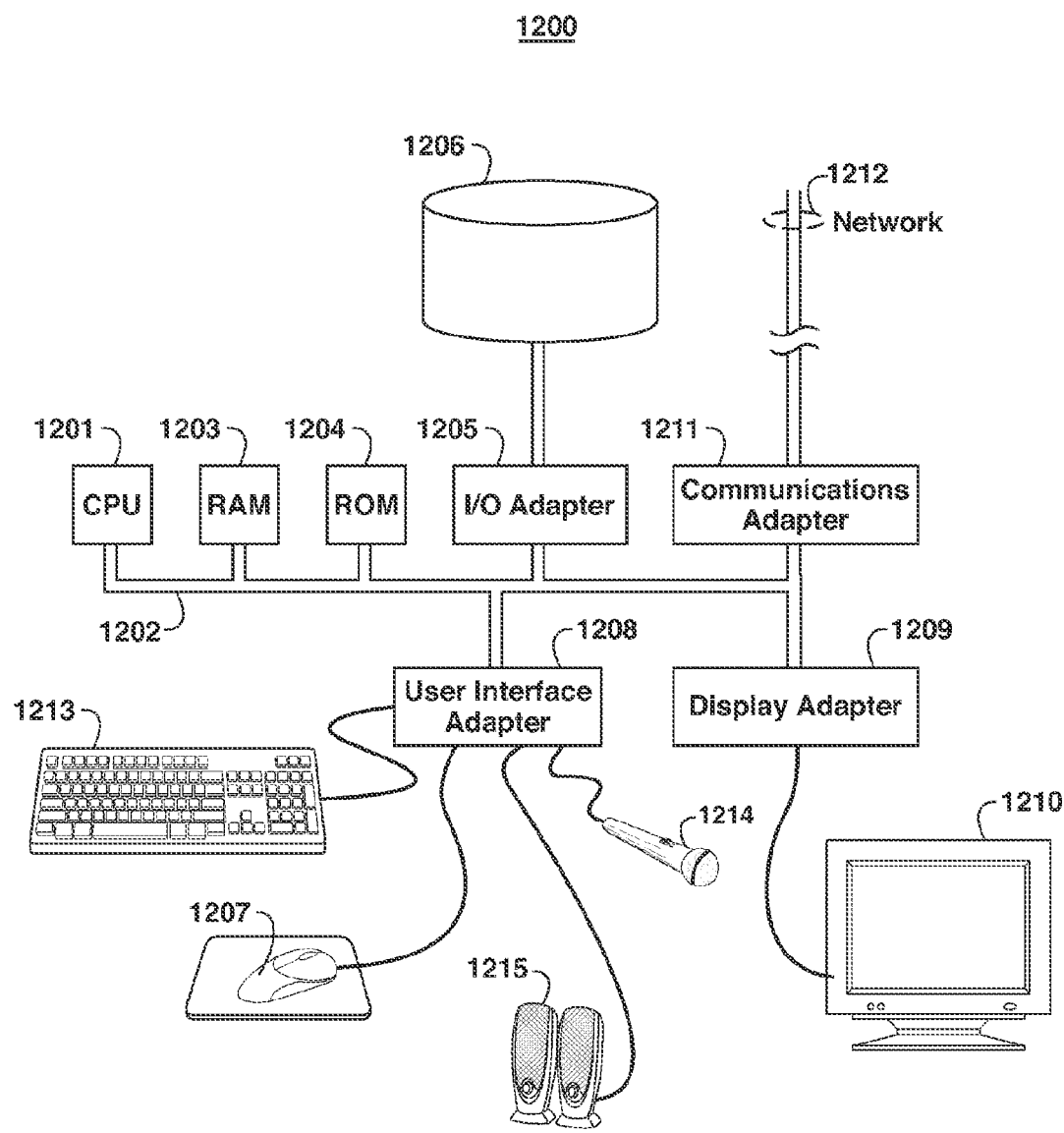
FIG. 12 illustrates an exemplary computer network that may be used to perform the method for predicting composition of petroleum as disclosed herein, and is discussed in greater detail below.

FIG. 12 illustrates an exemplary computer system 1200 on which software for performing processing operations of embodiments of the present invention may be implemented. A central processing unit (CPU) 1201 is coupled to system bus 1202. The CPU 1201 may be any general-purpose CPU. The present invention is not restricted by the architecture of CPU 1201 (or other components of exemplary system 1200) as long as CPU 1201 (and other components of system 1200) supports the inventive operations as described herein. The CPU 1201 may execute the various logical instructions according to embodiments. For example, the CPU 1201 may execute machine-level instructions for performing processing according to the exemplary operational flow described above in conjunction with FIG. 10. For instance, CPU 1201 may execute machine-level instructions for performing operational block 1006 of FIG. 10, as an example.

The computer system 1200 also preferably includes random access memory (RAM) 1203, which may be SRAM, DRAM, SDRAM, or the like. The computer system 1200 preferably includes read-only memory (ROM) 1204 which may be PROM, EPROM, EEPROM, or the like. The RAM 1203 and the ROM 1204 hold user and system data and programs, as is well-known in the art. The computer system 1200 also preferably includes an input/output (I/O) adapter 1205, a communications adapter 1211, a user interface adapter 1208, and a display adapter 1209. The I/O adapter 1205, the user interface adapter 1208, and/or communications adapter 1211 may, in certain embodiments, enable a user to interact with computer system 1200 in order to input information.

The I/O adapter 1205 preferably connects to a storage device(s) 1206, such as one or more of hard drive, compact disc (CD) drive, floppy disk drive, tape drive, etc. to computer system 1200. The storage devices may be utilized when the RAM 1203 is insufficient for the memory requirements associated with storing data for operations of embodiments of the present invention. The data storage of the computer system 1200 may be used for storing information and/or other data used or generated in accordance with embodiments of the present invention. The communications adapter 1211 is preferably adapted to couple the computer system 1200 to a network 1212, which may enable information to be input to and/or output from system 1200 via such network 1212 (e.g., the Internet or other wide-area network, a local-area network, a public or private switched telephony network, a wireless network, any combination of the foregoing). The user interface adapter 1208 couples user input devices, such as a keyboard 1213, a pointing device 1207, and a microphone 1214 and/or output devices, such as a speaker(s) 1215 to the computer system 1200. The display adapter 1209 is driven by the CPU 1201 to control the display on a display device 1210 to, for example, display information or a representation pertaining to a portion of a subsurface region under analysis, such as displaying a generated 3D representation of a target area, according to certain embodiments.

It shall be appreciated that the present invention is not limited to the architecture of system 1200. For example, any suitable processor-based device may be utilized for implementing all or a portion of embodiments of the present invention, including without limitation personal computers, laptop computers, computer workstations, and multi-processor servers. Moreover, embodiments may be implemented on application specific integrated circuits (ASICs) or very large scale integrated (VLSI) circuits. In fact, persons of ordinary skill in the art may utilize any number of suitable structures capable of executing logical operations according to the embodiments.

While the present invention may be susceptible to various modifications and alternative forms, the exemplary embodiments discussed above have been shown only by way of example. However, it should again be understood that the invention is not intended to be limited to the particular embodiments disclosed herein. Indeed, the present invention includes all alternatives, modifications, and equivalents falling within the true spirit and scope of the appended claims.

What is claimed is:

1. A computer-implemented method for predicting petroleum expulsion, the method comprising:
   isolating kerogen from a rock matrix;
   determining a chemical composition of the kerogen via a cheminal analysis;
   identifying a plurality of expelled products of the kerogen under geologic heating rates based on the determined chemical composition of the kerogen;
   grouping the plurality of expelled products into a plurality of product lumps based on their chemical composition;
   predicting petroleum expulsion from a subsurface formation for each of the plurality of product lumps, wherein the petroleum expulsion prediction is based on one or more expulsion kinetic models generated from the rate of expulsion of a specific product lump that is expressed by a single frequency factor and a discrete spectrum of activation energies;
   predicting products of secondary cracking reactions by trapping individual specific product lumps, identifying a plurality of expelled products of the individual specific product lumps under geologic heating rates; and deriving one or more secondary cracking kinetic models; and
   determining composition of expelled and thermally altered petroleum within basin evolution with a computer based at least partially on the one or more expulsion kinetic models and the one or more secondary cracking kinetic models.

2. The method for predicting petroleum expulsion recited in claim 1, comprising computing petroleum expulsion at a plurality of varying heating rates.

3. The method for predicting petroleum expulsion recited in claim 1, comprising defining a production rate curve for each of the plurality of product lumps.

4. The method for predicting petroleum expulsion recited in claim 1, comprising defining a plurality of stoichiometric coefficients for each of the plurality of product lumps.

5. The method for predicting petroleum expulsion recited in claim 1, wherein predicting petroleum expulsion comprises employing a theoretical model that is based on polymer theory to define the amount of bitumen that is dissolved in a kerogen matrix and Flory-Rehner Regular Solution theory that defines which molecules are retained and which are expelled.

6. The method for predicting petroleum expulsion recited in claim 1, comprising comparing predicted petroleum expulsion to known data.

7. The method for predicting petroleum expulsion recited in claim 6, comprising redefining the chemical structure if the predicted petroleum expulsion is outside a specified range with respect to the known data.

8. The method for predicting petroleum expulsion recited in claim 1, comprising preparing an outline of secondary cracking reactions.

9. The method for predicting petroleum expulsion recited in claim 1, wherein predicted petroleum expulsion comprises a quantity of expelled petroleum.

10. The method for predicting petroleum expulsion recited in claim 1, wherein predicted petroleum expulsion comprises timing data regarding petroleum expulsion.

11. The method of claim 1, wherein the chemical structure of the kerogen is defined based on a chemical structure-chemical yields modelling (CS-CYM) process.

12. The method of claim 1, wherein the secondary cracking reactions are modelled based on a chemical structure-chemical yields modelling (CS-CYM) process.

13. The method of claim 1, wherein the product lumps include
   a $C_1$ product lump,
   a $C_2$-$C_5$ product lump,
   a $C_6$-$C_{14}$ Aromatics product lump, and
   a $C_6$-$C_{14}$ Saturates product lump.

14. The method of claim 13, wherein the product lumps further include
   a $C_{15+}$ Saturates product lump,
   a $C_{15+}$ Aromatics product lump, and
   a $C_{15+}$ Polars product lump.

15. A method for producing hydrocarbons from a petroleum field, the method comprising:
- isolating kerogen from a rock matrix;
- determining a chemical composition of the kerogen via a chemical analysis;
- identifying a plurality of expelled products of the kerogen under geologic heating rates based on the determined chemical composition of the kerogen;
- grouping the plurality of expelled products into a plurality of product lumps based on their chemical composition;
- predicting petroleum expulsion from a subsurface formation for each of the plurality of product lumps, wherein the petroleum expulsion prediction is based on one or more expulsion kinetic models generated from the rate of expulsion of a specific product lump that is expressed by a single frequency factor and a discrete spectrum of activation energies;
- predicting products of secondary cracking reactions by trapping individual specific product lumps, identifying a plurality of expelled products of the individual specific product lumps under geologic heating rates; and deriving one or more secondary cracking kinetic models; and
- determining composition of expelled and thermally altered petroleum within basin evolution with a computer based at least partially on the one or more expulsion kinetic models and the one or more secondary cracking kinetic models; and
- extracting hydrocarbons from the petroleum field at least partially based on the determined composition and the predicted petroleum expulsion.

16. The method for producing hydrocarbons recited in claim 15, comprising computing petroleum expulsion at a plurality of varying heating rates.

17. The method for producing hydrocarbons recited in claim 15, comprising defining a production rate curve for each of the plurality of product lumps.

18. The method for producing hydrocarbons recited in claim 15, wherein predicting petroleum expulsion comprises employing a theoretical model is based on polymer theory to define the amount of bitumen that is dissolved in a kerogen matrix and Flory-Rehner Regular Solution theory that defines which molecules are retained and which are expelled.

19. The method for producing hydrocarbons recited in claim 15, comprising comparing predicted petroleum expulsion to known data.

20. The method for producing hydrocarbons recited in claim 19, comprising redefining the chemical structure if the predicted petroleum expulsion is outside a specified range with respect to the known data.

21. The method for producing hydrocarbons recited in claim 15, comprising preparing an outline of secondary cracking reactions.

22. The method for producing hydrocarbons recited in claim 15, wherein predicted petroleum expulsion comprises a quantity of expelled petroleum.

23. The method for producing hydrocarbons recited in claim 15, wherein predicted petroleum expulsion comprises timing data regarding petroleum expulsion.

24. A tangible, non-transitory machine-readable medium, comprising:
- code adapted to define a chemical structure of a kerogen, wherein the chemical structure is defined by isolating the kerogen from a rock matrix;
- code adapted to determine a chemical composition of the kerogen via a chemical analysis;
- code adapted to identify a plurality of expelled products of the kerogen under geologic heating rates based on the determined chemical composition of the kerogen;
- code adapted to group the plurality of expelled products into a plurality of product lumps based on their chemical composition;
- code adapted to predict petroleum expulsion from a subsurface formation for each of the plurality of product lumps, wherein the petroleum expulsion prediction is based on one or more expulsion kinetic models generated from the rate of expulsion of a specific product lump that is expressed by a single frequency factor and a discrete spectrum of activation energies;
- code adapted to predict products of secondary cracking reactions by trapping individual specific product lumps, to identify a plurality of expelled products of the individual specific product lumps under geologic heating rates; and to derive one or more secondary cracking kinetic models; and
- code adapted to determine composition of expelled and thermally altered petroleum within basin evolution based at least partially on the one or more expulsion kinetic models and the one or more secondary cracking kinetic models.

* * * * *